(12) United States Patent
Abou Shousha et al.

(10) Patent No.: US 10,368,735 B2
(45) Date of Patent: Aug. 6, 2019

(54) METHOD AND SYSTEM FOR THREE-DIMENSIONAL THICKNESS MAPPING OF CORNEAL MICRO-LAYERS AND CORNEAL DIAGNOSES

(71) Applicant: UNIVERSITY OF MIAMI, Miami, FL (US)

(72) Inventors: Mohamed Abou Shousha, Pembroke Pines, FL (US); Amr Saad Mohamed Elsawy, Miami, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 15/868,856

(22) Filed: Jan. 11, 2018

(65) Prior Publication Data

US 2018/0192866 A1 Jul. 12, 2018

Related U.S. Application Data

(60) Provisional application No. 62/445,106, filed on Jan. 11, 2017.

(51) Int. Cl.
*G06K 9/00* (2006.01)
*A61B 3/00* (2006.01)
(Continued)

(52) U.S. Cl.
CPC .......... *A61B 3/0025* (2013.01); *A61B 3/1005* (2013.01); *A61B 3/14* (2013.01); *G06T 3/0068* (2013.01); *G06T 3/4038* (2013.01); *G06T 5/50* (2013.01); *G06T 7/0014* (2013.01); *G06T 7/11* (2017.01); *G06T 7/32* (2017.01); *G06T 7/60* (2013.01); *G06T 15/04* (2013.01); *G06T 2207/20216* (2013.01); *G06T 2207/30041* (2013.01)

(58) Field of Classification Search
None
See application file for complete search history.

(56) References Cited

U.S. PATENT DOCUMENTS

2009/0046248 A1* 2/2009 Niven .................. A61B 3/135
351/206
2011/0043661 A1 2/2011 Podoleanu
(Continued)

OTHER PUBLICATIONS

International Search Report issued in connection with PCT/US2018/013409.

(Continued)

*Primary Examiner* — Weiwen Yang
(74) *Attorney, Agent, or Firm* — Akerman LLP

(57) ABSTRACT

Techniques for improved diagnosis, treatment, and monitoring of corneal pathologies use enhanced mapping of the cornea or corneal regions, to develop three-dimensional mapping of corneal thickness, while retaining particular corneal micro-layer thickness data. Anterior and posterior surface identifications, along with surface apex determinations, are used for registration of segmentation of these micro-layers. 3D heat maps and bull's-eye maps are generated from resulting thickness date. The maps provided enhanced evaluation and diagnosis of a corneal pathologies, such as keratoconus, pellucid marginal degeneration, post-refractive surgery ectasia, keratoglobus, corneal transplant rejection and corneal transplant failed grafts, Fuchs dystrophy, corneal limbal stem cell deficiency, dry eye syndrome, and post-corneal collagen crosslinking evaluation.

27 Claims, 16 Drawing Sheets
(5 of 16 Drawing Sheet(s) Filed in Color)

(51) Int. Cl.
*A61B 3/14* (2006.01)
*A61B 3/10* (2006.01)
*G06T 7/11* (2017.01)
*G06T 7/60* (2017.01)
*G06T 3/40* (2006.01)
*G06T 3/00* (2006.01)
*G06T 7/32* (2017.01)
*G06T 7/00* (2017.01)
*G06T 5/50* (2006.01)
*G06T 15/04* (2011.01)

(56) References Cited

U.S. PATENT DOCUMENTS

| | | | |
|---|---|---|---|
| 2013/0128222 A1* | 5/2013 | Huang | A61B 3/1005 |
| | | | 351/206 |
| 2014/0049748 A1 | 2/2014 | Hee | |
| 2014/0300862 A1* | 10/2014 | Perez | A61B 3/102 |
| | | | 351/206 |
| 2015/0138504 A1 | 5/2015 | Korb et al. | |
| 2015/0138505 A1 | 5/2015 | Grenon et al. | |
| 2015/0230863 A1 | 8/2015 | Youngquist et al. | |
| 2016/0038021 A1 | 2/2016 | Bagherinia et al. | |
| 2016/0228000 A1 | 8/2016 | Spaide | |
| 2016/0242639 A1* | 8/2016 | Ehlers | A61B 3/102 |
| 2018/0092534 A1 | 4/2018 | Nabhan | |

OTHER PUBLICATIONS

Written Opinion of the International Searching Authority issued in connection with PCT/US2018/013409.
Office Action dated Apr. 12, 2019 in related U.S. Appl. No. 16/269,549, 25 pages.

\* cited by examiner

RAW IMAGE OF THE CORNEA

REGISTERED AND AVERAGED IMAGE
OF THE CORNEA (USING 25 FRAMES)

LEGEND

C1: CENTRAL SUPERIOR
C2: CENTRAL INFERIOR
M1: MIDDLE SUPERIOR NASAL
M2: MIDDLE SUPERIOR
M3: MIDDLE SUPERIOR TEMPORAL
M4: MIDDLE INFERIOR TEMPORAL
M5: MIDDLE INFERIOR
M6: MIDDLE INFERIOR NASAL
O1: PERIPHERAL SUPERIOR NASAL
O2: PERIPHERAL SUPERIOR
O3: PERIPHERAL SUPERIOR TEMPORAL
O4: PERIPHERAL INFERIOR TEMPORAL
O5: PERIPHERAL INFERIOR
O6: PERIPHERAL INFERIOR NASAL

METHOD AND SYSTEM FOR THREE-DIMENSIONAL THICKNESS MAPPING OF CORNEAL MICRO-LAYERS AND CORNEAL DIAGNOSES

CROSS-REFERENCE TO RELATED APPLICATION

This application claims the benefit of U.S. Provisional Application No. 62/445,106, filed Jan. 11, 2017, entitled "Method And System For Three-Dimensional Thickness Mapping Of Corneal Micro-Layers And Corneal Diagnoses," which is hereby incorporated by reference in its entirety.

STATEMENT OF GOVERNMENT SUPPORT

This invention was made with government support under Grant No. K23EY026118 awarded by the National Eye Institute. The Government has certain rights in the invention.

FIELD OF THE INVENTION

The present disclosure relates to measuring corneal thickness and, more particularly, to measuring thickness of corneal micro-layers and developing a thickness mapping of the cornea for diagnostic purposes.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

There are many conditions that affect the eye. Some common conditions, for example, include aqueous deficiency and evaporative dry eye syndrome (DES), corneal ectasia, corneal limbal stem cell deficiency, keratoplasty graft rejection episode and failure, and Fuchs' dystrophy. However, conditions such as these are difficult to diagnose and treat.

Dry Eye Syndrome: Dry eye syndrome (DES) is a worldwide public health problem. In the United States alone, an estimated 25 million patients suffer from DES. DES adversely affects vision and causes constant symptoms of dryness, eye irritation, and foreign body sensation and thus negatively impacts patients' quality of life. Severe DES can lead to corneal melting compromising the integrity of the eye and can cause blindness. DES can be classified into aqueous deficiency DES or evaporative DES. In aqueous deficiency DES, there is deficiency in the quantity of tears secreted by the lacrimal glands. Whereas, in evaporative dry eye, which is caused by meibomian gland dysfunction (MGD), the problem lies in deficiency in the lipid layer of the tear film leading to excessive evaporation of the tears. The diagnosis and treatment of DES has become a challenge. Major research is directed at finding new remedies for DES but those efforts are limited by the fact that there is no gold standard for the diagnosis of DES. Available diagnostic tests lack standardization and usually are not representative of patient symptoms, in addition to other limitations.

The medical literature has shown poor association between current dry eye test and patient symptoms. Additionally, the current tests are poorly standardized tests as they are affected by factors that are difficult to control. For example, tear breakup time is affected by temperature and humidity of the examination room. Moreover, reflex lacrimation as the patient keeps his or her eyes open to obtain measurements can invalidate obtained measurements. The Schirmer test (in which paper strips are inserted into the eye to measure moisture production) is invasive and unpleasant to the patient. Further, hanging filter paper from a patient's eyes could result in reflex tearing that can affect obtained measurements. Fluorescein or other vital stains of the ocular surface are examples of tests that detect the injurious effect of DES on the ocular surface epithelium; however, results of those tests are identified using a slit lamp with magnification of only up to 16×. Such accuracy might be enough to diagnose moderate to severe dry eye, but certainly would not be enough to detect mild cases or monitor response to treatment. Indeed, the discrepancy between signs and symptoms of dry eye patients most likely stems from a lack of accuracy. Corneal nerves are sensitive enough to detect microscopic injuries to the ocular surface, but the available tests are not sensitive enough to visualize that injury or quantify it. Another limitation of current clinical techniques is that many are subjectively evaluated. What an examiner would consider mild corneal and conjunctival fluorescein staining, another could consider moderate and vice versa.

Diagnostic modalities have been recently introduced such as confocal microscopy and tear film osmolarity. Using confocal microscopy to diagnose DES is a time-consuming procedure that requires contact with the ocular surface and that makes it difficult to incorporate into everyday clinics and limits its use to research. Furthermore, it can only capture images over a small area of the total cornea. Tear film osmolarity has shown promise as a quantitative method to diagnose DES, but it is also invasive and time consuming. The literature has also shown lack of a cut off tear osmolarity values and a great overlap between normal subjects and DES patients. Until enough data proves otherwise, lubricating a dry eye would be able to improve the health of the ocular surface by providing an alternative to the inadequate natural tears, but does not alter the tear film osmolarity. Thus, looking at the osmolarity might not provide an insight about the response of the patient to treatment.

Corneal ectasia is a progressive disease that adversely affects the structural integrity of the cornea. The weakened cornea bulges, and crippling irregular astigmatism starts to develop. The astigmatism degrades vision and as the disease progresses, scarring of the cornea occurs. Corneal ectasia includes keratoconus, pellucid marginal degeneration, post-refractive surgery ectasia, and other rare diseases such as keratoglobus. Modalities for the treatment of corneal ectasia have been developed, such as corneal collagen cross-linkage that uses ultraviolet (UV) light and Riboflavin to stiffen the cornea and halt the progression of the disease. It is desirable to halt the progression of the disease at a very early stage, before vision is degraded by irregular astigmatism or scarring. Therefore, there is a need for a specific and sensitive sign that can detect those early patients to allow treatment before irreversible corneal damage occurs.

Post-refractive surgery ectasia is a devastating complication of refractive surgery, an elective procedure received by millions of patients in the United States alone. The most common cause of this complication that threatens vision in those patients is performing the refractive surgery on an early ectasia patient who was not detected by the conventional current diagnostic techniques. This highlights the need for a specific and sensitive sign that can be used to detect those early patients to save them from such a devastating complication.

Corneal topography and thickness are among the current diagnostic criteria of ectasia. Their use is complicated by their variations among the general populations. Normal range of corneal thicknesses is wide, and overlapping between normal thin corneas and early ectasia patients complicates the use of this criterion in the diagnosis of early cases of ectasia. Thus, lack of specificity is a significant limitation of using corneal thickening for the diagnosis of the ectasia. Corneal topography use in diagnosis of ectasia shares the same limitations as corneal thinning Irregular astigmatism is seen in normal subjects and in ectasia patients complicating its use to make the diagnosis, especially in mild cases.

Keratoplasty Graft Rejection/Failure and Fuchs' Dystrophy: Keratoplasty, or corneal transplantation, is used to replace a damaged or diseased cornea with a donated corneal tissue graft. About 60,000 corneal transplants are performed every year in the United States alone, it is not uncommon for a graft recipient's body to reject the donated corneal tissue. In fact, it is estimated that 50% of those patients will experience at least one episode of rejection, and 20% of transplants will ultimately fail by the third year, commonly due to the patient's immune system attacking the graft endothelium and destroying it. To preserve the graft and prolong its survival, rejection must be detected and reversed as early as possible. Unfortunately, however, the early stages of rejection are not easily identified. Currently, methods such as slit-lamp examination are used to detect rejection, but this method offers only limited magnification and mild subclinical rejection episodes are often missed. Further, performing endothelial cell count using specular microscopy lacks sufficient reproducibility, sensitivity, and specificity. Finally, measuring the central cornea thickness lack sufficient sensitivity to make it useful in the diagnosis of mild cases, and the wide range of normal corneal thickness complicates it use for diagnosis of mild corneal graft rejection and edema.

Fuchs' dystrophy (or Fuchs' endothelial dystrophy) is a degenerative disease of the corneal endothelium with accumulation of guttae (focal outgrowths) from the endothelial surface of the cornea. Degeneration of the corneal endothelial cells in Fuchs' dystrophy leads to corneal edema and vision loss. Although the disease is most common in people in their 50s and 60s, Fuchs' dystrophy can begin to affect people while in their 30s and 40s, so it is important to accurately identify the condition in its early stages. The same commonly used methods of detecting corneal graft rejection are often used to diagnose Fuchs' dystrophy, but these methods have the same limitations as discussed above. Additionally, there is no cut-off value that can define rejection, failure, or Fuchs' dystrophy. Similarly, using endothelial cell count is equally imprecise, as there is no cut-off value for endothelial cell count. The number of endothelial cells that can maintain a clear cornea is unknown. Further, it has been shown that reliable endothelial cell count is not possible in at least one third of Fuchs' dystrophy patients.

Fuchs' dystrophy is the leading cause of corneal transplantation in the United States, accounting for almost a quarter of all keratoplasties. About 5% of the United States population older than 40 years has Fuchs' dystrophy. This condition is an aging disease and as our population ages, the prevalence of Fuchs' dystrophy is expected to rise even more and is thus expected to impose an even more significant public health problem. Fuchs' dystrophy imposes challenge on eye banking. The confusion between normal subjects and early Fuchs' dystrophy carries the risk of either transplanting patients with early Fuchs' dystrophy corneal grafts or, on the other hand, the unnecessary wasting of corneal tissue. Further, the demand on corneal tissue is growing. The aging of the population, the increased prevalence of Fuchs' dystrophy, and the lowered threshold for endothelial keratoplasty are widening the gap between the demand and the supply. However, developing de novo corneal guttae in corneal grafts has been reported, which is most likely an effect of transplanting undiagnosed Fuchs' dystrophy grafts.

Limbal stem cell deficiency of the cornea is another concern. Limbal stem cells are responsible for repopulating the corneal epithelium. Deficiency in the stem cell of the cornea leads to failure of the epithelium to renew or repair itself. This results in epithelial defects of the cornea that is persistent and resistant to treatment and loss of the corneal clarity leading to blindness. The basal epithelial layer of the cornea is the innermost layer of epithelial cells that is produced by those stem cells and is a precursor of the more superficial layers of the corneal epithelium. The diagnosis of limbal stem cell deficiency (LSCD) is currently done using the slit lamp which uses up to a magnification of only 16× and is unable to visualize the limbal stem cells nor the basal epithelial layer. Confocal microscopy is able to visualize the basal layer of the epithelium but through a very small window (0.4 mm×0.4 mm) and that is not representative of the cornea as a whole. It is also not possible to construct cross-sectional view of those cell layers.

Optical coherence tomography (OCT) is a noninvasive optical signal acquisition and processing method that captures micrometer-resolution, three-dimensional images from within, for example, biological tissue. OCT has proven to be an indispensable tool for imaging the retina and the optic nerve. It has changed the practice of ophthalmology and has become the gold standard for diagnosis and management of diseases with significant morbidity and prevalence such as age-related macular degeneration and glaucoma. Nevertheless, OCT has not yet achieved such a role in anterior segment in general and cornea imaging in particular. This is most likely due to the lack of standardized clinical applications for the device in imaging the anterior segment and cornea.

It is therefore desirable to provide improved indices for diagnosing corneal conditions such as dry eye syndrome, corneal ectasia, keratoplasty rejection and failure, and Fuchs' dystrophy. It is further desirable that these improved indices be usable with current and future imaging devices such as OCT systems, or any other imaging device or system capable of providing high-resolution images of the eye and in particular the cornea, for identifying and monitoring corneal conditions.

SUMMARY OF THE INVENTION

The present techniques provide a method and system for improved diagnosis, treatment, and monitoring of certain corneal conditions, in addition to the evaluation of new treatments. The present techniques are directed to enhanced mapping of the cornea, in particular developing a layer differentiating three-dimensional mapping of corneal thickness, while retaining layer thickness data. The techniques provide a heretofore unavailable rendering of the diagnostic data, for example, corneal layer thickness, thereby providing enhanced evaluation and diagnosis of a number of conditions, including keratoconus, pellucid marginal degeneration, post-refractive surgery ectasia, keratoglobus, corneal transplant rejection and corneal transplant failed grafts, Fuchs dystrophy, corneal limbal stem cell deficiency, and dry eye syndrome (DES).

In an example, a computer-implemented method of evaluating an eye, the method comprises: segmenting, using an image processor, a plurality of high-resolution images of a cornea of the eye, to identify one or more of the plurality of biologically-defined micro-layers of the cornea, the plurality of high-resolution images comprising a plurality of images for a plurality of biologically-defined micro-layers of the cornea; determining thickness data for each of the identified one or more of the plurality of biologically-defined micro-layers, from the segmentation of the plurality of high-resolution images; developing, from the thickness data for each of the identified one or more of the plurality of biologically-defined micro-layers, a thickness map, the thickness map identifying differences in corneal thickness across the identified biologically-defined micro-layer, wherein the thickness map is correlated to a diagnosable condition of the cornea; and displaying the thickness map to provide an indication of the diagnosable condition.

In some examples, the biologically-defined micro-layers comprise an epithelium, a basal epithelial layer, a Bowman's layer, one or more Endothelial/Descemet's layers complex, and/or a collagen crosslinking layer.

In some examples, the diagnosable condition is selected from the group consisting of keratoconus, pellucid marginal degeneration, post-refractive surgery ectasia, corneal transplant rejection and corneal transplant failed grafts, Fuchs dystrophy, corneal stem cell deficiency and dry eye syndrome.

In some examples, the mapping is a three-dimensional thickness map. In some examples, the thickness map is a heat map indicating differences in corneal micro-layer thicknesses. In some examples, the thickness map is a bull's-eye thickness map.

In some example, method comprises developing a three-dimensional thickness map of the Bowman's layer, the thickness map having a color coding that differentiates minimum thickness regions of the Bowman's layer, normal thickness regions of the Bowman's layer, maximum thickness regions of the Bowman's layer, and/or irregularities in the thickness regions across the Bowman's layer.

In some examples, the method further comprises developing a three-dimensional thickness map of Endothelium/Descemet's layer, the thickness map having a color coding that differentiates minimum thickness regions of the Endothelium/Descemet's layer, normal thickness regions of the Endothelium/Descemet's layer, maximum thickness regions of the Endothelium/Descemet's layer, and/or irregularities in the thickness regions across one or more layers.

In some examples, the method further comprises developing a three-dimensional thickness map of the corneal epithelium, wherein the thickness map includes an irregularity indication of changes in thickness across the corneal epithelium, wherein the irregularity indication indicates differences in concentration of thickness irregularities across different regions of the cornea.

In some examples, the method further comprises developing a three-dimensional thickness map of basal epithelial layer, the thickness map having a color coding that differentiates the presence, absence, normal thickness regions of the basal epithelial layer, and/or irregularities in the thickness regions across one or more layers.

In another example, a system for evaluating a diagnosable condition of an eye, the system comprises: one or more processors; a computer-readable memory storing non-transient instructions that when executed by the one or more processors cause the system to: segment, using an image processor, a plurality of high-resolution images of a cornea of the eye, to identify one or more of the plurality of biologically-defined micro-layers of the cornea, the plurality of high-resolution images comprising a plurality of images for a plurality of biologically-defined micro-layers of the cornea; determine thickness data for each of the identified one or more of the plurality of biologically-defined micro-layers, from the segmentation of the plurality of high-resolution images; develop, from the thickness data for each of the identified one or more of the plurality of biologically-defined micro-layers, a thickness map, the thickness map identifying differences in corneal thickness across the identified biologically-defined micro-layer, wherein the thickness map is correlated to a diagnosable condition of the cornea; and display the thickness map to provide an indication of the diagnosable condition.

In some examples, the computer-readable memory stores further non-transient instructions that when executed by the one or more processors cause the system to: (a) perform an image registration on the plurality of high-resolution images by (i) identifying an anterior surface of one of the plurality of biologically-defined micro-layers of the cornea, the anterior surface being a registration reference surface, (ii) comparing a plurality of image frames in the plurality of high-resolution images to the anterior surface, (iii) extracting frames that do not satisfy a registration condition, and (iv) for the remaining frames performing a summation and averaging process to produce a high-resolution composite image of the one of the plurality of biologically-defined micro-layers.

In some examples, the computer-readable memory stores further non-transient instructions that when executed by the one or more processors cause the system to: (b) identify one or more contrast transition surfaces for the high-resolution composite image, the transition surfaces corresponding to interfaces between the different corneal micro-layers; (c) perform (a) for an adjacent biologically-defined micro-layer to identify a second high-resolution composite image, the adjacent biologically-defined micro-layer being identified by the one or more contrast transition surfaces; and (d) perform (c) for each biologically-defined micro-layer of the cornea. In some examples, (b) is performed to identify a transition to an anterior interface of the epithelium, an epithelium/basal epithelial layer interface, a basal epithelium/Bowman's interface, Bowman's/stroma interface, an anterior interface of the endothelial/Descemet's layers, an interface of the endothelial/Descemet's layers, an aqueous humor, and/or a collagen crosslinking layer interface.

In some examples, the computer-readable memory stores further non-transient instructions that when executed by the one or more processors cause the system to: (a) perform an image registration on the plurality of high-resolution images by, for each of the plurality of high-resolution images, (i) identifying an anterior surface of the cornea and a posterior surface of the cornea, and (ii) matching the anterior surface of the cornea and the posterior surface of the cornea to an anterior surface and a posterior surface, respectively, of a reference frame; and (b) perform a summation and averaging process to produce a high-resolution composite image from the registered plurality of high-resolution images, where the high-resolution composite image is of the cornea.

In some examples, the computer-readable memory stores further non-transient instructions that when executed by the one or more processors cause the system to: perform the image registration on the plurality of high-resolution images by identifying an apex of the cornea and matching the apex of the cornea to an apex of a reference frame.

In some examples, the computer-readable memory stores further non-transient instructions that when executed by the one or more processors cause the system to: identify an anterior surface and a posterior surface of the high-resolution composite image; flatten the high-resolution composite image using the anterior surface; flatten the high-resolution composite image using the posterior surface; estimate one or more biologically-defined micro-layers of the cornea from the flattening using the anterior surface; estimate one or more the biologically-defined micro-layers of the cornea from the flattening using the posterior surface; and generate a segmented high-resolution composite image by combining the estimating from the flattening using the anterior surface with the estimating from the flattening using the posterior surface.

In some examples, the computer-readable memory stores further non-transient instructions that when executed by the one or more processors cause the system to: estimate the one or more biologically-defined micro-layers of the cornea from the flattening using the anterior surface by performing a vertical projection of the flattening using the anterior surface and identifying one or more contrast transition surfaces corresponding to interfaces between the one or more biologically-defined micro-layers; and estimate the one or more biologically-defined micro-layers of the cornea from the flattening using the posterior surface by performing a vertical projection of the flattening using the posterior surface and identifying one or more contrast transition surfaces corresponding to interfaces between the one or more biologically-defined micro-layers.

In another example, a system for a diagnosable condition of an eye, the system comprises: one or more processors; a computer-readable memory storing non-transient instructions that when executed by the one or more processors cause the system to: perform a two-surface registration on each of a plurality of high-resolution images of the cornea, the plurality of high-resolution images comprising a plurality of images for a plurality of biologically-defined micro-layers of the cornea, and generate a high-resolution composite image of the cornea, wherein the two-surface registration comprises an anterior surface registration and a posterior surface registration; segment the high-resolution composite image to identify each of the plurality of biologically-defined micro-layers of the cornea, wherein segmentation of the high-resolution composite image comprises flattening the high-resolution composite image and performing a vertical projection of a flattened rendition of the high-resolution composite image to produce a segmented high-resolution composite image; determine the thickness of at least one of the plurality of biologically-defined micro-layers of the cornea from the segmented high-resolution composite image; develop a thickness map for at least one of the plurality of biologically-defined micro-layers of the cornea, the thickness map identifying visual differences in thickness across the at least one of the plurality of biologically-defined micro-layers, wherein the thickness map is correlated to a diagnosable condition of the cornea; and display the thickness map to provide a visual indication of the diagnosable condition.

In another example, a system for a diagnosable condition of an eye, the system comprises: one or more processors; a computer-readable memory storing non-transient instructions that when executed by the one or more processors cause the system to: generate a high-resolution composite image of the cornea from a plurality of high-resolution images of the cornea using a multiple surface registration on the plurality of high-resolution images of the cornea, the plurality of high-resolution images comprising a plurality of images for a plurality of biologically-defined micro-layers of the cornea, the plurality of high-resolution images of the cornea each being curved images with an apex; segment the high-resolution composite image to identify each of the plurality of biologically-defined micro-layers of the cornea using a multiple surface flattening on the high-resolution composite image, the segmentation generating a segmented high-resolution composite image; determine the thickness of at least one of the plurality of biologically-defined micro-layers of the cornea from the segmented high-resolution composite image; develop a thickness map for the at least one of the plurality of biologically-defined micro-layers of the cornea, the thickness map identifying visual differences in thickness across the at least one of the plurality of biologically-defined micro-layers; and display the thickness map.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

The figures described below depict various aspects of the system and methods disclosed herein. It should be understood that each figure depicts an example of aspects of the present systems and methods.

FIG. 2A illustrates a three-dimensional heat map of healthy corneal tissue. FIG. 2B illustrates a three-dimensional bull's-eye map of healthy corneal tissue.

FIG. 3A illustrates a three-dimensional heat map of a keratoconus condition. FIG. 2B illustrates a three-dimensional bull's-eye map of the keratoconus condition.

DETAILED DESCRIPTION

Figure 1:
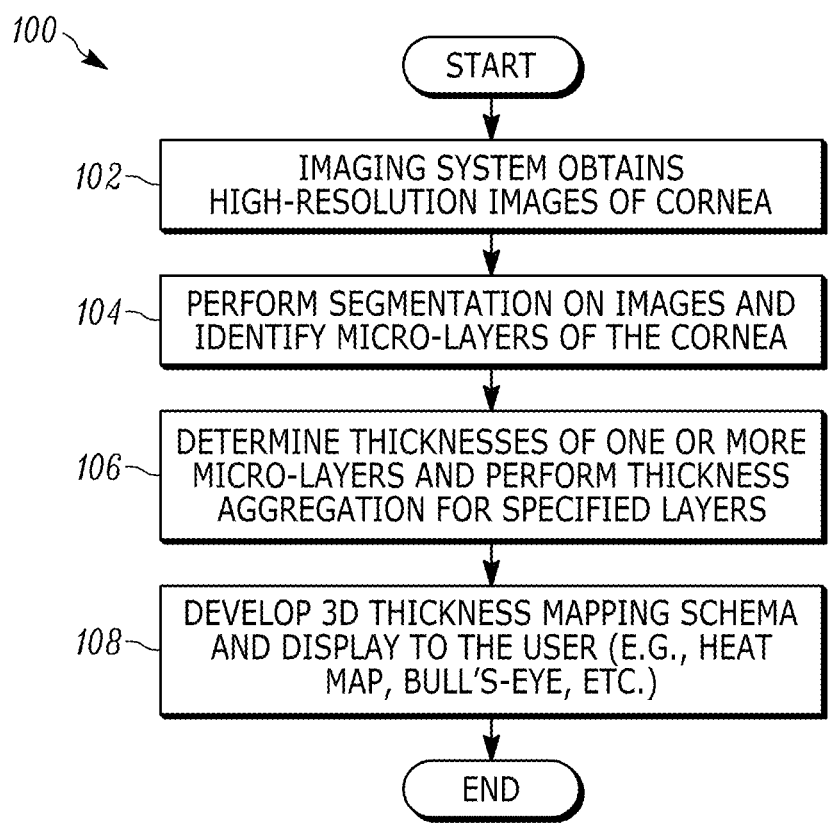
FIG. 1 illustrates a process for evaluating the eye of a subject, in particular, the cornea of a subject through developing a three-dimensional thickness map of one or more micro-layers of the cornea, in accordance with an example.

FIG. 1 illustrates an example computer-implemented method 100 of evaluating the eye of a subject and, in particular, for evaluating the corneal condition for the eye. The method 100 is adapted to evaluate corneal conditions including keratoconus, pellucid marginal degeneration, post-refractive surgery ectasia, keratoglobus, corneal transplant rejection and corneal transplant failed grafts, Fuchs dystrophy, corneal limbal stem cell deficiency and dry eye syndrome (DES).

The method 100 may be implemented by a system, such as that describe further below in reference to FIG. 7. In the illustrated example, at operation 102, an optical imaging system obtains a plurality of high-resolution images of a cornea of the eye(s) of a subject. These high-resolution images may be captured in real-time, for example. In other examples, the images may be previously collected corneal images stored in an image database or other memory.

Whether the optical imaging system itself records the corneal images directly from the subject or whether the corneal images are obtained from another imager or from a database, the image processing, analysis, and diagnostic techniques herein may be implemented partly or wholly within an existing optical imaging system or partly or wholly within a dedicated image processor. Example optical imaging systems include suitable corneal imagers such as charge-coupled device (CCD) cameras, corneal topography scanners using optical slit designs, such as the Orbscan system (Bausch & Lomb, Rochester, N.Y.), Scheimpflug imagers such as the Pentacam (Oculus, Lynnwood, Wash.), conventional microscopes collecting reflected light, confocal microscope-based systems using a pinhole source of light and conjugate pinhole detector, optical coherence tomography (OCT) imagers imaging the cornea and anterior segment imagers, optical interferometry-based systems in which the light source is split into the reference and measurement beams for corneal image reconstruction, and high-frequency high-resolution ultrasound biomicroscopy (UBM) imagers.

The corneal images may be a plurality of images each captured with the eye looking in a different direction, from which a wide scan of the cornea is formed by stitching images together. In some examples, the images are a plurality of wide scan images of the cornea collected from a wide angle optical imaging system, where the wide angled images are corrected for optical distortion, either through image processing or through a corrective optic stage in the imaging system.

In examples, the obtained images contain images of one or more biologically-definable micro-layers of the cornea. Such images would typically be un-segmented, raw cornea image data, meaning that the micro-layers would not be identified directly in the images, but rather the images would capture one or more micro-layers that are segmented by the imaging system applying the unique algorithm techniques herein.

At operation 104, the method 100 performs a segmentation process on the plurality of high-resolution images. In particular, an image process identifies, via the segmenting the images, one or more of a plurality of biologically-defined micro-layers of the cornea. From the segmentation, the image processor determines the thickness for the one or more biologically-defined micro-layers of the cornea. The image processor, also referred to herein as an imaging system, may be a processor of an existing optical imaging system, such as an OCT imager, while in some examples, that image processor is in a separate system that receives the high-resolution images from the optical imaging system. The image processor may be implemented on a general purpose processor or on a dedicated processor, by way of example.

The image processor, at operation 104, may be programmed to identify each of the plurality of biologically-defined micro-layers, i.e., an epithelium, a basal epithelial layer, a Bowman's layer, and one or more endothelial/Descemet's layers complex. In other examples, such as when the imaging system is programmed to identify for a particular corneal condition, the image processor, at operation 104, may segment the images and identify the thickness of only certain micro-layers of the cornea.

With the micro-layers segmented into different image data, and the thicknesses of the micro-layers determined at operation 104, at operation 106, the image processor combines the image data for each of the plurality of biologically-defined micro-layers of the cornea and produces a thickness map of the total corneal thickness (whole cornea from one limbus to the other). That is, in some examples, the thickness map is a summation of the determined thicknesses for each of the plurality of biologically-defined micro-layers, illustrating collective thickness across the cornea, e.g., providing a 3D map of the whole cornea from one limbus to the other. Further, the combinational data in the thickness map may retain specified thickness values for each of the micro-layers. That is, the techniques measure the thickness of the corneal micro-layers all across the entire cornea from one end to the other.

The ability to determine thickness across the cornea allows for measuring regions of abnormal or irregular thickness across the entire cornea. But the determinations at operations 104 and 106 also allow the image processor to analyze micro-layer thicknesses as well, thus providing two levels of thickness analysis, a first overall corneal thickness and a second, micro-layer thickness.

In the illustrated example, at operation 108, the imaging system develops a thickness map and displays the thickness map through a monitor (or display) via operation 108. That thickness map may visually identify differences in thickness of corneal micro-layers across the thickness map, by visually depicting the overall corneal micro-layer thicknesses. The visual depiction identifies differences in thicknesses that are correlated to diagnosable conditions of the cornea.

Figure 2A:
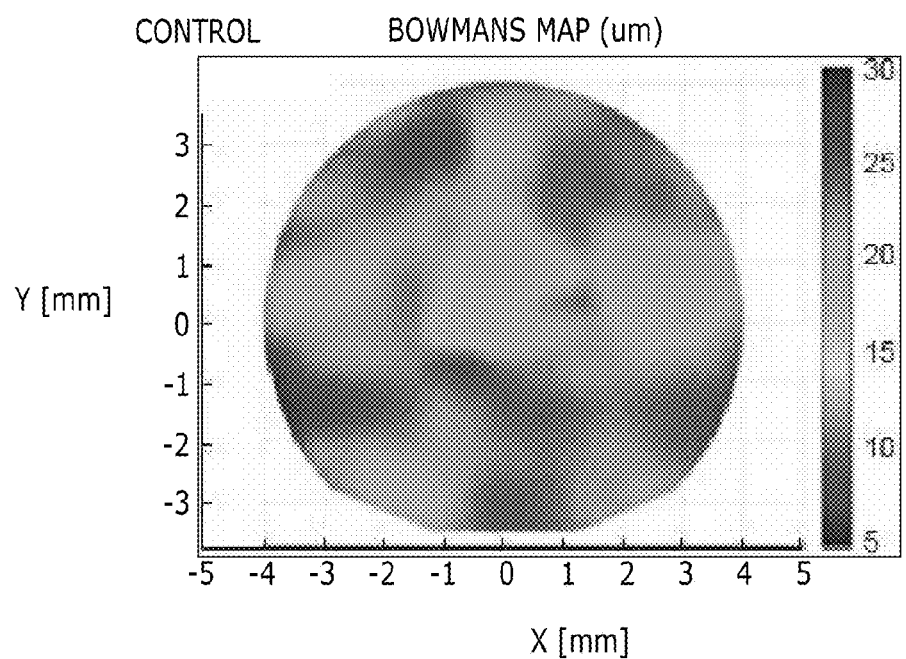
FIGS. 2A and 2B illustrate three-dimensional maps developed by the process of FIG. 1 for a subject with healthy corneal tissue.

FIG. 2A illustrates example thickness map depiction of a corneal micro-layer, specifically a heat map of the Bowman's layer. The heat map shows variations in color as coded by color or shading. The heat map legend is based on the obtained normative thickness data of corneal microlayers, using green for normal, and yellow for borderline, and red for pathology. As the thinning of the basal epithelial and Bowman's layer is pathological, we used red color to represent the pathological thinning and yellow as the borderline thinning, whereas green was the normal range thickness. In Endothelial/Descemet's layers complex, thickening of the layer is the pathological change. Thus, we used red to represent the pathological thickening based on the normative data obtained, yellow for borderline thickness and green for normal thickness.

Figure 2B:
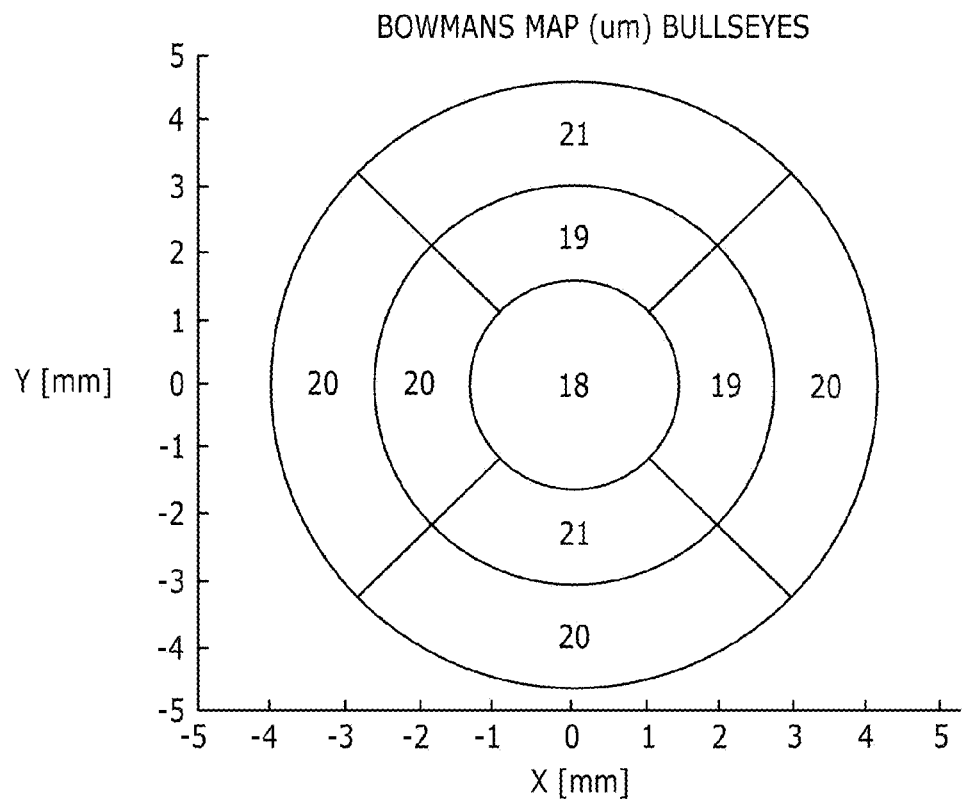

In the illustrated example, the thickness values were determined to extend from at or about 5 microns to at or about 30 microns over the entire Bowman's layer of the cornea. FIG. 2B illustrates another thickness map of the same Bowman's layer, but in the form of a bull's-eye thickness map.

The heat map and bull's-eye maps are examples of different three-dimensional thickness map schemas that may be generated through the present techniques. Further as discussed herein, for each of these types of thickness map schemas there are numerous variants, e.g., a bull's-eye map may illustrate values for the thicknesses of a micro-layer or that bull's-eye map may illustrate ratios of thicknesses between regions of a micro-layer.

The bull's-eye map displays the thickness map of the Bowman's layer as a series of thickness values for 9 sections of the layer: one central region centered around the pupil, and eight wedge shaped regions extending radially outward from the central region. The bull's-eye map can be presented in different mapping schema, e.g., by dividing the cornea into multiple regions and presenting the average, minimal or maximum thickness data, or the ratio of thickness of a micro-layer to the total corneal thickness at each region of the cornea. In other examples schema, the bull's-eye map is presented as a ratio of the thickness of a micro-layer in a region of the cornea to the thickness measured of the micro-layer in another corneal region. In yet other example schema, the bull's-eye map is presented as a ratio of the thickness of the micro-layer in a specific region of the cornea compared to normative data for that region or for that micro-layer. Such mapping schema can also show the progression of thickness or thickness profile of the micro-layer from the center to the periphery of the cornea along different meridians of the cornea.

The thickness maps of FIGS. 2A and 2B represent the thickness values in the Bowman's layer for a control sample, i.e., a healthy subject's Bowman's layer. Generally, the thickness values across the Bowman's layer range from 12 microns to 30 microns in thickness; although other thickness ranges may exist for certain subjects and subject populations.

Figure 3A:
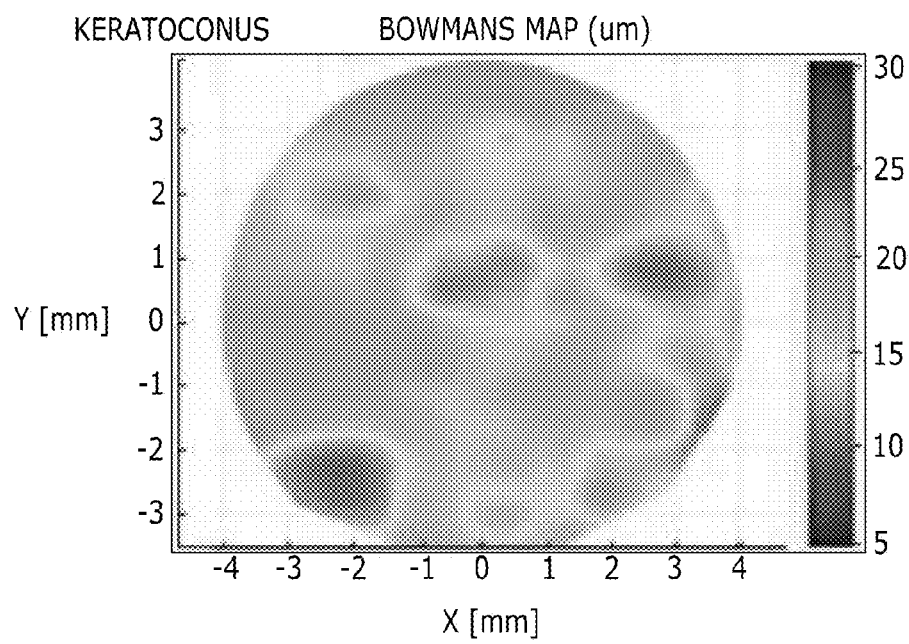
FIGS. 3A and 3B illustrate three-dimensional maps developed by the process of FIG. 1 for a subject with keratoconus.
Figure 3B:
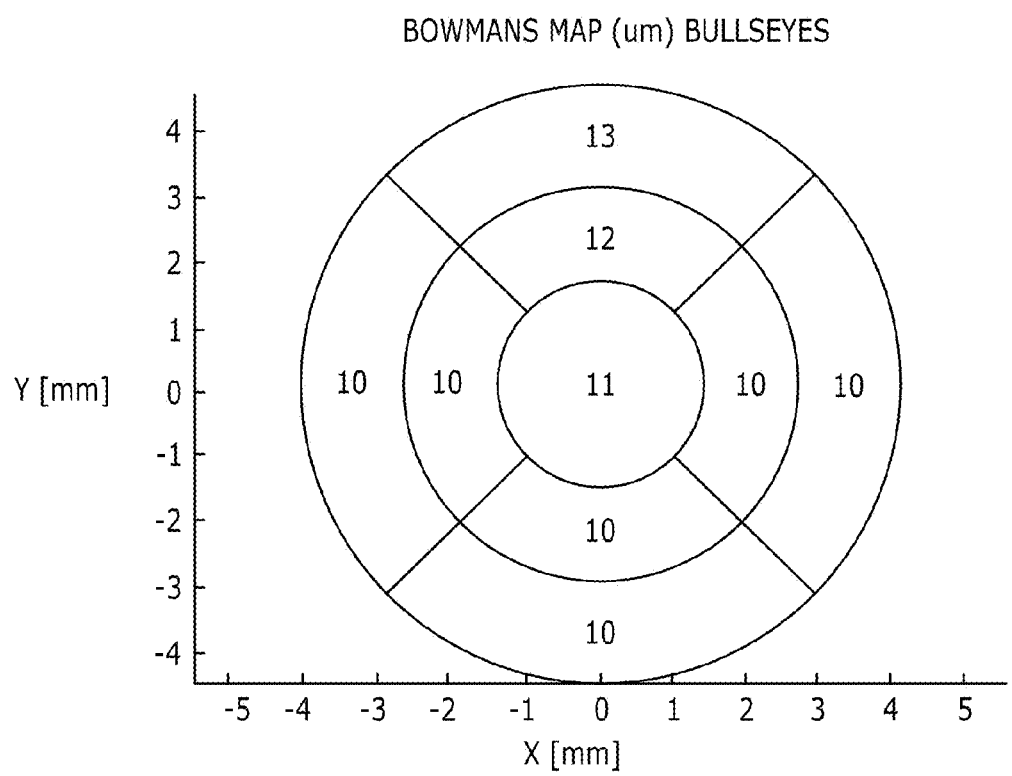

FIGS. 3A and 3B illustrate thickness maps developed by the method 100 from corneal images of a subject that has keratoconus. The keratoconus is identifiable from the thickness mapping of the Bowman's layer, using a number of different diagnostic determinations of the system. The system, for example, may compare the thickness maps of FIG. 3A or 3B to the corresponding thickness maps of FIG. 2A or 2B, and determine thickness difference values across all or certain regions of the Bowman's layer. While pixel-to-pixel comparisons may be performed, generally these comparisons would be region-to-region.

Figure 11:
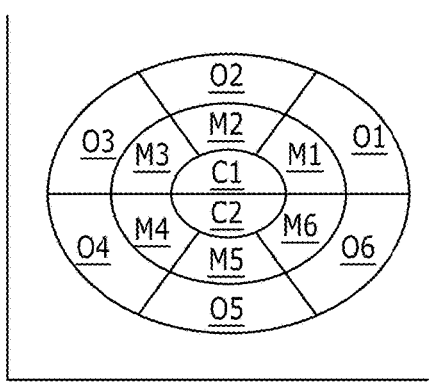
FIG. 11 illustrates a legend for a bull's-eye mapping thickness map, in accordance with an example.
Figure 12A:
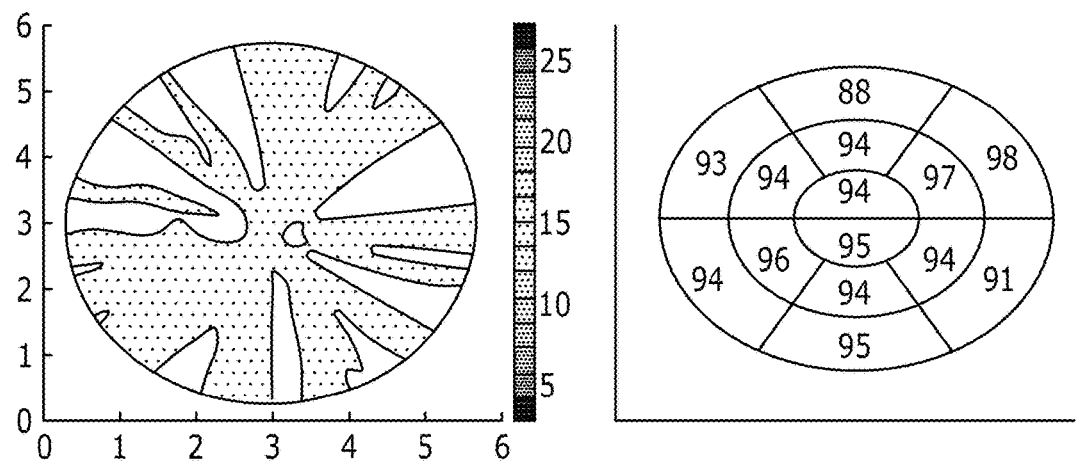
FIG. 12A illustrates a three-dimensional heat map of a Bowman's layer and a bull's-eye map using the mapping schema of FIG. 11, both for a normal, healthy subject, in accordance with an example.
Figure 12B:
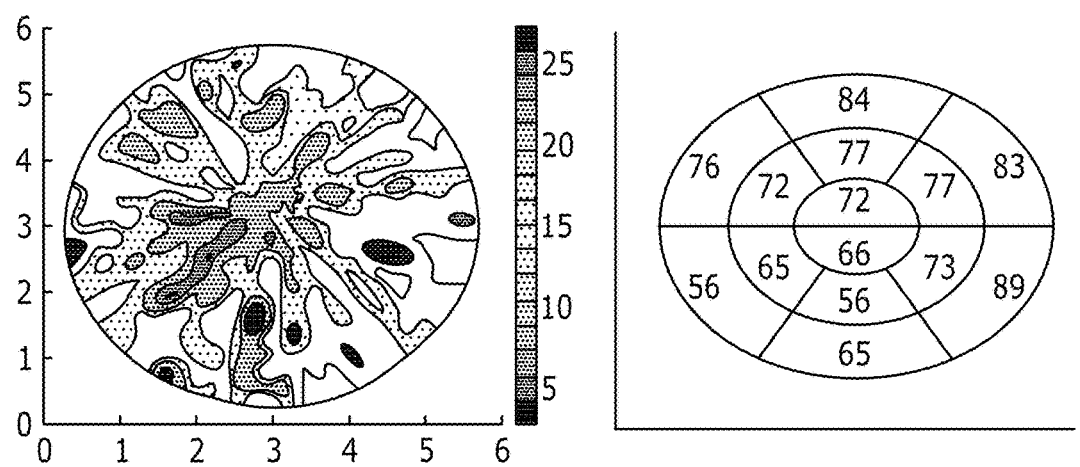
FIG. 12B illustrates a similar three-dimensional heat map of Bowman's layer and a bull's-eye map, for a subject with keratoconus, in accordance with an example.

In some examples, the system may determine a composite index value for the Bowman's layer and compare that composite index to a composite index value determined for the control thickness map. For example, indices such as (A) a Bowman's ectasia index (3D BEI; defined as Bowman's layer (BL) minimum thickness of each region of the inferior half of the cornea divided by BL average thickness of the corresponding region of superior half of the cornea, multiplied by 100) and (B) a BEI-Max (defined as BL minimum thickness of the inferior half of the cornea divided by BL maximum thickness of the superior half of the cornea multiplied by 100) may be used for comparison. An example determination of a 3D BEI is taking the minimum thickness of BL in region C1 divided by the mean thickness of BL region C2, multiplied by 100 (see, e.g., the bull's-eye thickness map and legend of FIG. 11 and heat map and bull's-eye example of FIGS. 12A and 12B, respectively). With the present techniques, described herein, such indices are calculated, by the system, using the 3D map of the entire cornea allowing more accurate indexes and index comparisons. The use of 3D BEI demonstrates considerable advantages over conventional techniques. For example, with the present techniques, we can detect the thinnest point on the entire cornea not just the thinnest point on a 2D scan that goes through a central area of the cornea but might miss the corneal Bowman's thinnest point.

In yet other examples, the system compares the thickness maps of FIGS. 3A and 3B against stored threshold thickness values, either overall thickness values of the layer or threshold thickness values of one or more of the regions in the bull's-eye map. In either case, the amount of difference in thickness, whether between different heat maps or bull's-eye maps or between thickness maps and threshold data or thickness progression profile, may be further examined using an assurance process that determines if the differences are substantial enough to satisfy a desired assurance level for making a diagnosis. The imaging system may perform an assurance process that not only examines the amount of difference between current corneal images and a control or threshold, but examines particular regions within the Bowman's layer, as thickness differences in certain regions may be more correlative to keratoconus than thickness differences in other examples. Indeed, in some examples, primary regions of interest for diagnosable conditions such as keratoconus may be programmed into the imaging system, regions such as inferior cornea. In other examples, however, the imaging system may be programmed using a learning mode, whether a machine learning algorithm is applied to multiple sets of corneal image data until the machine learning algorithm identifies from the data—the data would include a variety of images for subjects with normal cornea tissue and a variety of images for subjects with keratoconus. From the machine learning, primary regions of interest may be identified, as well as thickness difference values across the different regions. For the latter, for example, the imaging system, may not only determine different threshold thicknesses for different regions in a layer, but the system may determine different high-assurance values for those different regions. For example, assessing the bull's-eye plot of FIG. 2B against other image data, an imaging system may identify a threshold of 20 microns for each of two opposing radial medial, lateral and inferior regions of the cornea. But as shown in FIG. 3A, only one of the inferior radial regions shows a great correlation to indicating keratoconus. The imaging system, applying the machine learning, can then determine a threshold of 20 microns for each region, but apply a broader assurance band for the left-most region, thereby not flagging a larger number of thickness variations below that threshold, because the region appears less correlative, and thereby less expressive, of keratoconus. The right-most region, however, could be determined to have a very narrow assurance band, meaning that for the same threshold, thickness values below but very close to the threshold would be flagged by the system as indicating, or at least possibly indicating, keratoconus.

The example maps of FIGS. 2A, 2B, 3A, and 3B are determined from thickness maps for the Bowman's layer and used to diagnosis keratoconus, in particular. The same techniques may be used to develop a thickness mapping for any one or more of the corneal micro-layers, whichever layers are expressive of the diagnosable condition under examination, including, but not limited to, keratoconus, pellucid marginal degeneration, post-refractive surgery ectasia, corneal transplant rejection and corneal transplant failed grafts, Fuchs dystrophy, limbal stem cell deficiency and dry eye syndrome. The conditions keratoconus, pellucid marginal degeneration, and post-refractive surgery ectasia are particularly expressed by the Bowman's layer. Therefore, the method 100 may be applied to determine a thickness mapping for that Bowman's layer. Other conditions would result from analyzing the thickness of other micro-layers in the cornea. Indeed, the present techniques may be used to determine thicknesses and generate thickness maps for all of these micro-layers of the cornea through the same automated process.

In the illustrated example, at operation 108, the imaging system generates a three-dimensional thickness map. The heat map, i.e., FIGS. 2A and 3A, expresses the third dimensional (the XY area being the first two dimensions) thickness data in a color coding or gray scale coding. The bull's-eye map, i.e., FIGS. 2B and 3B, expresses the third dimension using a numerical thickness score. That numerical thickness score represents an overall thickness value for the region of the bull's-eye map. That value may be an aggregated thickness value summing the thicknesses over the entire region. That value may be an average thickness value over the entire region, minimal, maximum, variance or standard deviation thickness value over the entire region, or some other thickness value, ratio of the thickness of the region to another region or to a diagnostic index.

Whichever mapping schema is used, the three-dimensional thickness map developed by the system is configured to differentiate normal thickness areas in the heat map (or regions in the bull's-eye) from thicknesses that express the diagnosable condition. In the illustrated example, the thickness maps further indicate the minimum and maximum thicknesses with the Bowman's layer.

In some examples, multiple different thickness maps may be used to analyze and diagnose the same diagnosable condition. For example, when the condition is dry eye syndrome, a thickness map (or maps) may be generated analyzing the thickness for a plurality of different micro-layers that includes the epithelium, the basal epithelial layer, the Bowman's layer, and the Endothelial/Descemet's layers complex of the cornea. In such examples, the three-dimensional thickness map would include combined thicknesses for all these layers summed together. However, depending on the data set and the differences in thicknesses for certain layers, only one of these layers, e.g., the epithelium, may be used. For example, while overall thickness for all these layers combined can indicate dry eye, particular irregularities in the thickness of the epithelium may also indicate dry eye syndrome. That is, different thickness patterns in the epithelium may themselves be an expressive biomarker of dry eye syndrome. For example, the imaging system may assess the thickness map(s) of the corneal epithelium and analyze a central are (or central region of the bull's-eye) of the cornea which indicates that the dry eye condition results from aqueous deficiency. In another example, the imaging system analyzes the thickness map(s) of the epithelium, in particular a lower or upper area (or region) of the cornea which indicates that lipid deficiency is the cause of the dry eye syndrome. The imaging system may detect and analyze irregularities through a number of different processes. For example, calculating the standard deviations and variance of the epithelial thickness on each region of a thickness map (e.g., on each region of a bull's-eye map) will identify irregularities. Such irregularities may be determined for one or more key regions within a thickness map or, in other examples, across the entire thickness map. Which regions and which amounts of irregularities (e.g., the amount of variance) that are analyzed may depend on the underlying condition, with certain conditions associated with certain amounts of irregularities, over certain regions of a thickness map, and for only certain micro-layers. As such, the imaging system may be configured to identify for a pre-specified irregularity pattern over a micro-layer. While in other examples, the imaging system may analyze the entire cornea for identification of any of a plurality of irregularity patterns, thereafter identifying to medical professionals which diagnosable conditions have been identified for the subject. Other statistical analyses can be applied to further refine the irregularity pattern identification. Further still, in yet other examples, thickness maps for micro-layers may be compared to thickness values of an imaginary regular surface to identify variation patterns.

Other diagnosable conditions include limbal stem cell deficiency, which is diagnosable from the presence of basal epithelial cells thinning or the absence of basal epithelial cells. In such examples, a thickness map of the basal epithelial layer is performed and the results diagnosed.

Thus, in some examples, the method 100 may be used to obtain images of a subject using an OCT machine or other imaging device that gives high resolution cross-sectional images of the cornea. The subject may be instructed to look at different fixation targets representing the different directions of gaze, and the machine will capture images of different segments of the cornea. In other examples, the images may be captured using a wide angle lens that provides a wide view of the cornea. The machine or other image processor will segment the corneal micro layers, including for example the epithelium, basal epithelial layer, Bowman's layer, and endothelial/Descemet's layers. In some examples, the segmentation may be presented to the machine operator to allow the operator to review the segmented images and make changes as appropriate. The machine or other image processor will then calculate the thicknesses of the layers from all obtained images, including the epithelium, basal epithelial layer, Bowman's layer, and endothelial/Descemet's layers. The machine or other image processor will stitch the data obtained from the obtained images and combine them to produce a wide color coded thickness map of the total corneal thickness, epithelium, basal epithelial layer, Bowman's layer, and endothelial/Descemet's layers. The machine or other image processor will create bull's-eye thickness maps and will compute the diagnostic indices for keratoconus, pellucid marginal degeneration, post-refractive surgery ectasia, corneal transplant rejection and health, Fuchs dystrophy and dry eye syndrome.

In some examples where the diagnosable condition is Fuchs dystrophy and/or corneal graft, the machine or other image processor may produce a color coded 3D map of the entire Endothelium/Descemet's layer of the cornea. Relative thickening of the Endothelium/Descemet's layer and thickening and irregularity compared to a normal value will be highlighted on a color coded 3D. A separate bull's-eye map may be developed and will show the average thickness of the Endothelium/Descemet's layer in different parts of the cornea which is diagnostic for the condition. Progression or stability of the condition may be detected by comparison of serial maps and thickness data obtained from follow up maps.

In some examples where the diagnosable condition is keratoconus, pellucid marginal degeneration, and/or post-refractive surgery ectasia, the machine or other image processing machine will produce a color coded 3D map of the entire Bowman's layer. Relative thinning of the Bowman's layer and thinning compared to a normal value will be highlighted on the color coded map. A separate bull's-eye map will show the average and minimum thickness of the Bowman's layer in different parts of the cornea which are diagnostic for the condition. Progression or stability of the condition will be detected by comparison of serial maps and thickness data obtained from follow up maps.

In some examples where the diagnosable condition is dry eye patients, the machine or other image processor will create a color coded 3D map of the entire cornea and calculate the irregularities of the epithelium of the cornea. Relative irregularity compared to a normal value will be highlighted on the color coded map. A separate bull's-eye map will show the average thickness and the variation of the layer thickness in different parts of the cornea which is diagnostic for the condition. The machine or other image processor identifying more irregularities in the central part of the cornea thereby diagnosing aqueous deficiency, which diagnosis may be displayed to the operator, while more irregularities on the lower or upper part of the cornea are diagnosed by the machine or other image processor as lipid deficiency dry eye syndrome or Meibomian gland dysfunction, which may be displayed to the operator. Progression or stability of the condition will be detected by comparison of serial maps and thickness data obtained from follow up maps.

In some examples where the diagnosable condition is limbal stem cell deficiency, the machine or other image processor will generate a color coded 3D map of the entire the basal epithelial layer and then determine relative thinning or absence of the layer basal epithelial, which is diagnostic of limbal stem cell deficiency. If the condition is identified by the machine or other image processor, that diagnosis is displayed to the operator.

Figure 4:
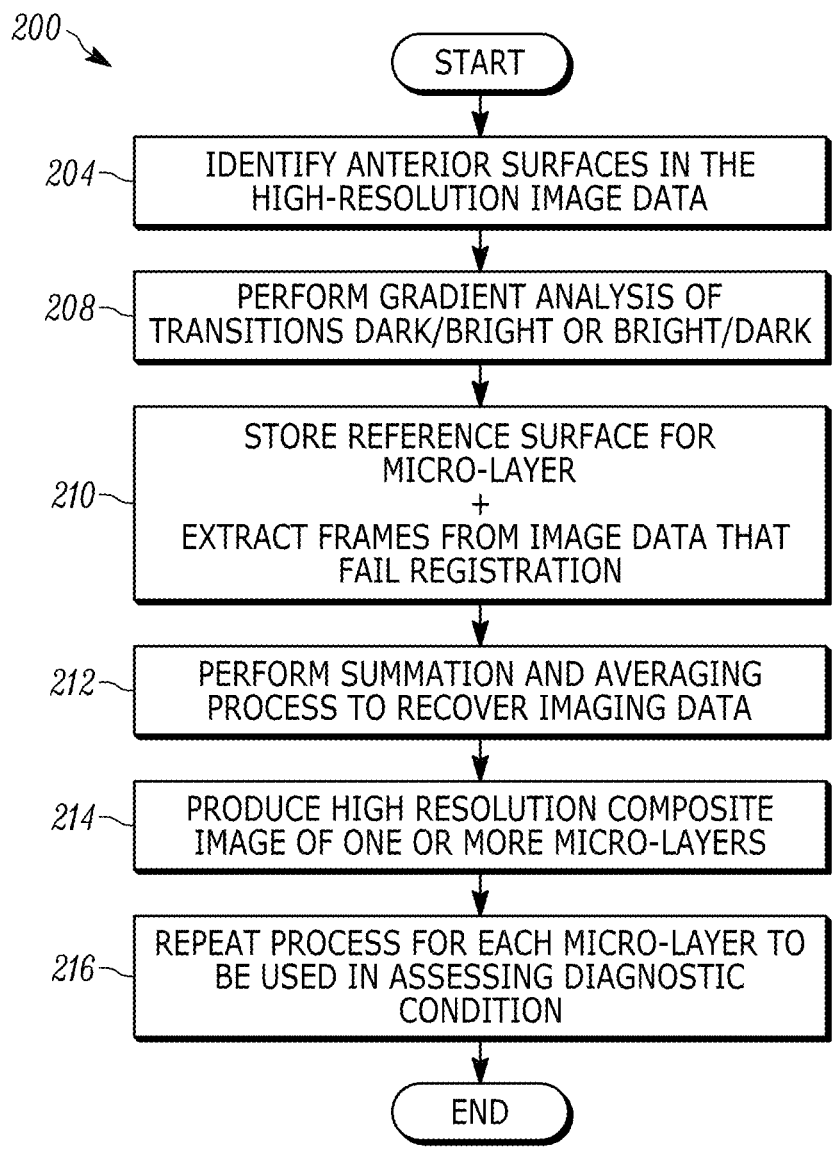
FIG. 4 illustrates an example process of segmentation and micro-layer identification and thickness determination, in accordance with an example.

FIG. 4 illustrates an example computer-implemented segmentation process 200 as may be implemented by 104 in FIG. 1. In the illustrated example, the high-resolution images are segmented to identify image data for one or more of the biologically-defined micro-layers. Initially, an optional image registration process is performed on the high-resolution images, in particular by identifying a series of surface layers that correspond to layers at which an image transitions from one micro-layer of the cornea to another micro-layer. The registration process may include, at an operation 204, identifying an anterior surface of one the micro-layers in the cornea. This anterior surface may be of any of the epithelium, basal epithelial layer, Bowman's layer, or endothelial/Descemet's layers complex, for example. In other examples, the anterior and posterior surfaces of the micro-layers may be identified.

The anterior surface can be identified using a contrast identification-based algorithm, for example, an algorithm identifying gradient changes from dark to bright or bright to dark, in an image. In an example, gradient method and graph theory techniques were adapted to the cornea and used to segment the corneal layers. Furthermore, in some examples, particular image filters are combined with the image analysis to more accurately identify transitions.

For example, image preprocessing is done in order to enhance the optical coherence tomography (OCT) images in order to facilitate automatic segmentation of corneal micro-layers and thickness data extraction, namely, the epithelium, basal epithelial layer, Bowman's layer, and endothelial/Descemet's layers. Preprocessing of the OCT images includes registration and averaging of the images to reduce noise to signal ratio and correct for patients' movements artifacts.

While not shown, the operation 204 may be followed by an averaging operation applied to the high-resolution images for reducing noise and improving image quality.

At an operation 208, a gradient analysis is performed on the received high-resolution images. That gradient analysis identifies gradient changes of a threshold amount, whether the gradient change is dark to bright or bright to dark, for example using a graph theory algorithm. In general, at operation 208, an automatic segmentation of the corneal micro-layers is achieved by detecting the interfaces between one layer from another layer. From the gradient changes, the anterior surface is identified and stored as the registered reference surface, at operation 210. In other examples, as described, the reference surface may be determined from analyzing an anterior surface and a posterior surface. The operation 210 may also perform alignment of subsequent images to this reference surface. That alignment may be done electronically through image processing instructions. The alignment may include side to side and/or rotational alignment. If the anterior surface in one or more of the frames does not fit other frames registered surface secondary to a course movement of the patient, that frame is extracted and excluded. This frame extraction is provided for each image that does not satisfy a registration condition.

Using the reference surface, the system may be programmed to select from the programmed alignment algorithms and apply the one or more algorithms to achieve a suitable registration and, in some examples, to achieve the best registration.

Every subsequent high-resolution image may be compared to the registered reference, and, after the operation 210 extracts those frames that do not satisfy the registration condition, at operation 212, images may be averaged over a certain cycle, e.g., after 25 frames, 50 frames, 100 frames, or more frames or less. That is, at operation 212, the process 200 applies to the remaining frames a summation and averaging process to produce, at operation 214, a segmented high-resolution composite image of the one of the plurality of biologically-defined micro-layers. The process 200 may repeat for each of the micro-layers in the cornea, via operation 216. For example, the operation 226 may repeat the process 200 identifying a plurality of contrast transition surfaces, where the transition surfaces correspond to interfaces of the micro-layers in the cornea. The process 200 may be repeated for micro-layers adjacent to any preceding surface, and this process may repeat until each biologically-defined micro-layer is mapped out.

In the illustrated example, segmentation occurs without initial registration, and instead, after the segmentation (e.g., micro-layer extraction of operation 210) applied to each image, the images may then be summed and averaged to produce the segmented high-resolution composite image. Other example implementations of the present techniques are provided in reference to FIGS. 8-10.

Figure 5A:
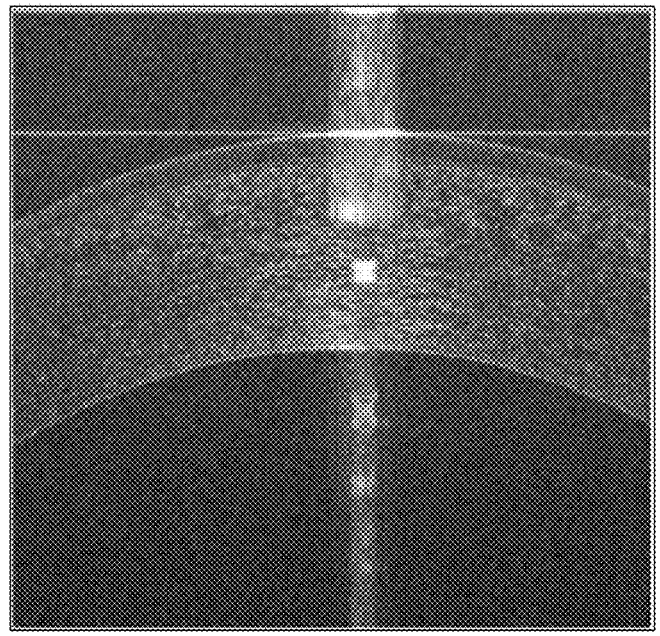
FIG. 5A is a cross-sectional image of a first raw high-resolution image of a cornea, in an example.
Figure 5B:
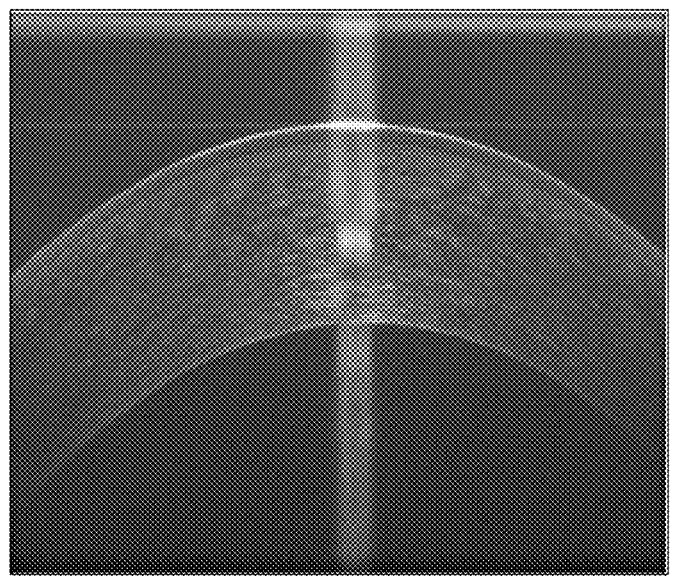
FIG. 5B is a cross-sectional image of registered and averaged images of the cornea, in an example.

FIG. 5A illustrates a first raw high-resolution image of a cornea. FIG. 5B illustrates registered and averaged images of the cornea, using 25 frames. From the comparing the two images, FIG. 5B illustrates the high contrast image, with the great certainly to visualize the corneal micro-layers.

Figure 6:
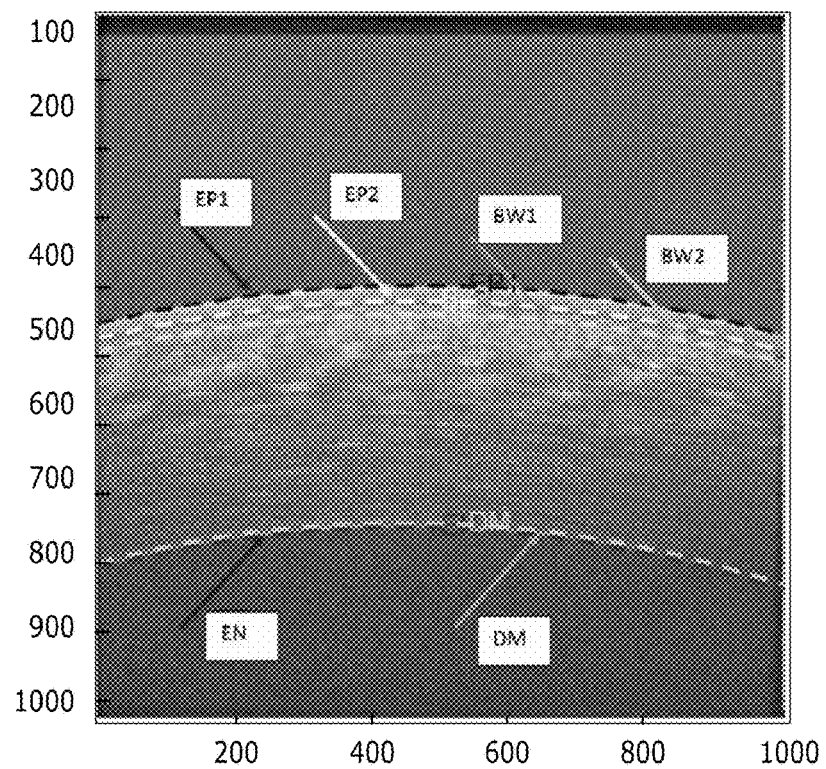
FIG. 6 is a cross-sectional image of an entire cornea with micro-layers mapped out and demarcated by their respective anterior surfaces for each layer. EP1 is the anterior surface of the corneal epithelium; EP2 is the interface between the basal epithelium and the remaining layers of the epithelium; BW1 is the interface between the basal epithelium and the Bowman's layer; BW2 is the interface between the Bowman's layer and the stroma; DM is the interface between the stroma and the Endothelial/Descemet's complex layer and the stroma; and EN is the posterior interface of the Endothelial/Descemet's complex layer.

FIG. 6 illustrates an entire cornea with micro-layers mapped out and demarcated by their respective anterior and posterior surfaces for each layer, in accordance with the process of FIG. 4. For the cornea Layers, the epithelium is the layer from EP1 to EP2, the basal epithelial layer is the layer from EP2 to BW1, the Bowman's layer is the layer from BW1 to BW2. The Endothelial/Descemet's layer is the layer from DM to EN.

Generally speaking, the process 200 may be used to identify a transition to an anterior interface of the epithelium, an epithelium/basal epithelial layer interface, a basal epithelium/Bowman's interface, Bowman's/stroma interface, an anterior interface of the endothelial/Descemet's layers, an interface of the endothelial/Descemet's layers, and an aqueous humor.

Figure 7:
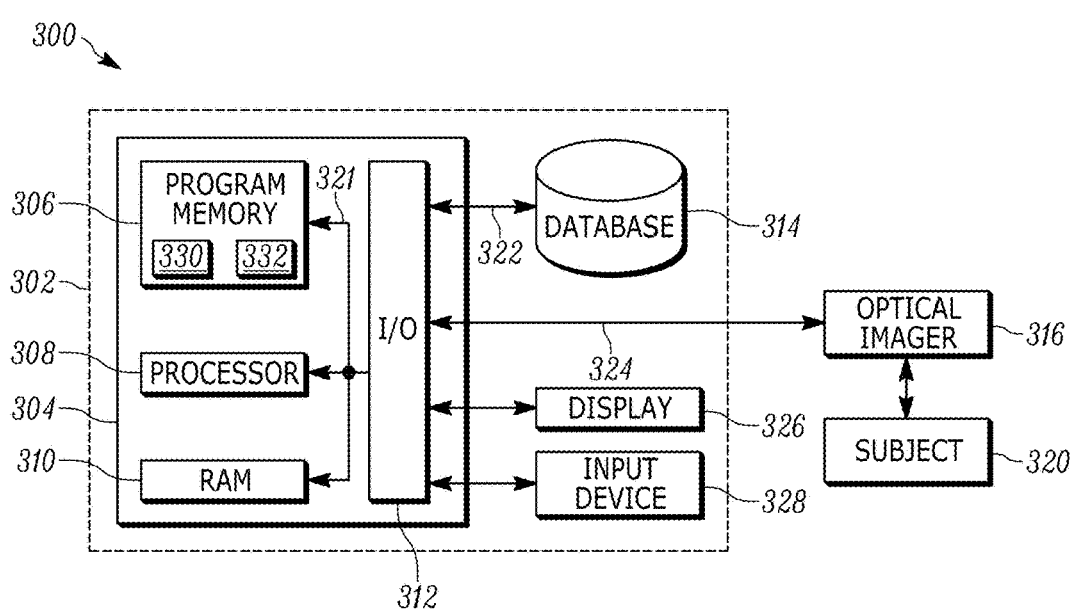
FIG. 7 is a schematic illustration of an example optical imaging system for performing thickness mapping of corneal micro-layers in performing the processes of FIGS. 1 and 4, in an example.

FIG. 7 illustrates an imaging system 300 illustrating various components used in implementing any of the techniques described herein. An image processing device 302 is coupled to a corneal optical imager 316 that collects high-resolution corneal images for a subject 320. The optical imager 316 may be any optical imaging system such as an OCT imager communicatively coupled to an image processing device 302, which may be a dedicated imaging system for example. In some examples, the imaging system 300 may be partly or wholly implemented on an optical imaging system, such as an OCT imager.

The optical imager 316 collects and stores corneal image data on the subject 120, as raw data, processed data, or pre-processed data.

In some examples, the system 300 is operable in a first mode, called a training mode, where the system 300 collects data and develops data on healthy corneal tissue.

In a second mode, called the analysis mode, the system 300 collects subsequent corneal tissue images and compares analyzed image data against the image data of healthy subjects captured in the training mode. Both the training mode data and the analysis mode data include generating the three dimensional thickness mapping data described herein.

In a healthy subject, training data may include data from a number of subjects compiled together as aggregated training data. In some examples, that aggregated training data is coded with demographic data, such that the system 300 may use demographic-specific subsets of that aggregated data when develop training models for a subject associated with a particular demographic group.

The optical imager 316 is communicatively connected to the image processing device 302 through a wired or wireless link 324. For the former, the optical imager 316 may capture and store corneal images, and a user or care provider may connect the optical imager 316 to the image processing device 302 through a Universal Serial Bus (USB), IEEE 1394 (Firewire), Ethernet, or other wired communication protocol device. The wireless connection can be through any suitable wireless communication protocol, such as, WiFi, NFC, iBeacon, etc.

The image processing device 302 may have a controller 304 operatively connected to a database 314 via a link 322 connected to an input/output (I/O) circuit 312. It should be noted that, while not shown, additional databases may be linked to the controller 304 in a known manner. The controller 304 includes a program memory 306, the processor 308 (may be called a microcontroller or a microprocessor), a random-access memory (RAM) 310, and the input/output (I/O) circuit 312, all of which are interconnected via an address/data bus 321. It should be appreciated that although only one microprocessor 308 is shown, the controller 304 may include multiple microprocessors 308. Similarly, the memory of the controller 304 may include multiple RAMs 310 and multiple program memories 306. Although the I/O circuit 312 is shown as a single block, it should be appreciated that the I/O circuit 312 may include a number of different types of I/O circuits. The RAM(s) 310 and the program memories 306 may be implemented as semiconductor memories, magnetically readable memories, and/or optically readable memories, for example. The link 324 operatively connects the controller 304 to the capture device 316, through the I/O circuit 312.

The program memory 306 and/or the RAM 310 may store various applications (i.e., machine readable instructions) for execution by the microprocessor 308. For example, an operating system 330 may generally control the operation of the image processing device 302 and provide a user interface to the device 302 to implement the processes described herein. The program memory 306 and/or the RAM 310 may also store a variety of subroutines 332 for accessing specific functions of the image processing device 302. By way of example, and without limitation, the subroutines 332 may include, among other things: obtaining, from an optical imaging system, a plurality of high-resolution images of a cornea of the eye; segmenting, using an image processor, a plurality of high-resolution images of a cornea of the eye, to identify one or more of the plurality of biologically-defined micro-layers of the cornea, the plurality of high-resolution images comprising a plurality of images for a plurality of biologically-defined micro-layers of the cornea; determining thickness data for each of the identified one or more of the plurality of biologically-defined micro-layers, from the segmentation of the plurality of high-resolution images; developing, from the thickness data for each of the identified one or more of the plurality of biologically-defined micro-layers, a thickness map, the thickness map identifying differences in corneal thickness across the identified biologically-defined micro-layer, wherein the thickness map is correlated to a diagnosable condition of the cornea; and displaying the thickness map to provide an indication of the diagnosable condition. In other examples, the subroutines 332 may include instructions to: segment, using an image processor, a plurality of high-resolution images of a cornea of the eye, to identify one or more of the plurality of biologically-defined micro-layers of the cornea, the plurality of high-resolution images comprising a plurality of images for a plurality of biologically-defined micro-layers of the cornea; determine thickness data for each of the identified one or more of the plurality of biologically-defined micro-layers, from the segmentation of the plurality of high-resolution images; develop, from the thickness data for each of the identified one or more of the plurality of biologically-defined micro-layers, a thickness map, the thickness map identifying differences in corneal thickness across the identified biologically-defined micro-layer, wherein the thickness map is correlated to a diagnosable condition of the cornea; and display the thickness map to provide an indication of the diagnosable condition. In other examples, the subroutines 332 may include instructions to: perform a two-surface registration on each of a plurality of high-resolution images of the cornea, the plurality of high-resolution images comprising a plurality of images for a plurality of biologically-defined micro-layers of the cornea, and generate a high-resolution composite image of the cornea, wherein the two-surface registration comprises an anterior surface registration and a posterior surface registration; segment the high-resolution composite image to identify each of the plurality of biologically-defined micro-layers of the cornea, wherein segmentation of the high-resolution composite image comprises flattening the high-resolution composite image and performing a vertical projection of a flattened rendition of the high-resolution composite image to produce a segmented high-resolution composite image; determine the thickness of at least one of the plurality of biologically-defined micro-layers of the cornea from the segmented high-resolution composite image; develop a thickness map for at least one of the plurality of biologically-defined micro-layers of the cornea, the thickness map identifying visual differences in thickness across the at least one of the plurality of biologically-defined micro-layers, wherein the thickness map is correlated to a diagnosable condition of the cornea; and display the thickness map to provide a visual indication of the diagnosable condition. In other examples, the subroutines 332 may include instructions to: generate a high-resolution composite image of the cornea from a plurality of high-resolution images of the cornea using a multiple surface registration on the plurality of high-resolution images of the cornea, the plurality of high-resolution images comprising a plurality of images for a plurality of biologically-defined micro-layers of the cornea, the plurality of high-resolution images of the cornea each being curved images with an apex; segment the high-resolution composite image to identify each of the plurality of biologically-defined micro-layers of the cornea using a multiple surface flattening on the high-resolution composite image, the segmentation generating a segmented high-resolution composite image; determine the thickness of at least one of the plurality of biologically-defined micro-layers of the cornea from the segmented high-resolution composite image; develop a thickness map for the at least one of the plurality of biologically-defined micro-layers of the cornea, the thickness map identifying visual differences in thickness across the at least one of the plurality of biologically-defined micro-layers; and display the thickness map. The subroutines 332 may include subroutines to executed any of the operations described herein, including for example those of FIGS. 1, 4, and 8-10.

The subroutines 332 may include other subroutines, for example, implementing software keyboard functionality, interfacing with other hardware in the device 302, etc. The program memory 306 and/or the RAM 310 may further store data related to the configuration and/or operation of the image processing device 302, and/or related to the operation of one or more subroutines 332. For example, the data may be data gathered from the system 316, data determined and/or calculated by the processor 308, etc.

In addition to the controller 304, the image processing device 302 may include other hardware resources. The device 302 may also include various types of input/output hardware such as a visual display 326 and input device(s) 328 (e.g., keypad, keyboard, etc.). In an embodiment, the display 326 is touch-sensitive, and may cooperate with a software keyboard routine as one of the software routines 332 to accept user input. It may be advantageous for the image processing device to communicate with a broader network (not shown) through any of a number of known networking devices and techniques (e.g., through a computer network such as an intranet, the Internet, etc.). For example, the device may be connected to a database of corneal image data, a database of healthy corneal image data, and a database of corneal image data for subjects experiencing one or more diagnosable conditions such as those listed herein above.

Figure 8:
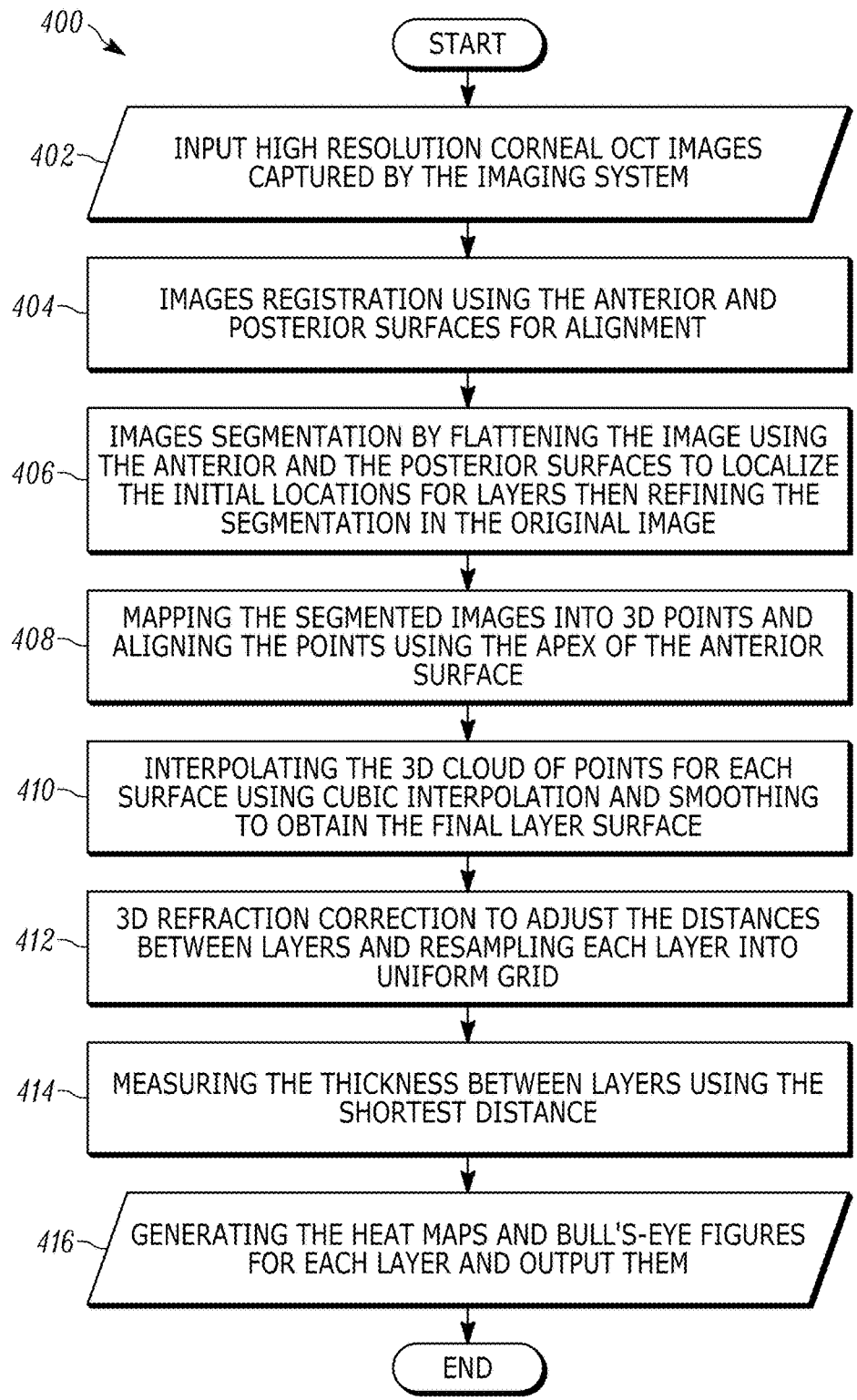
FIG. 8 illustrates a process for evaluating the eye of a subject, in another example.
Figure 9:
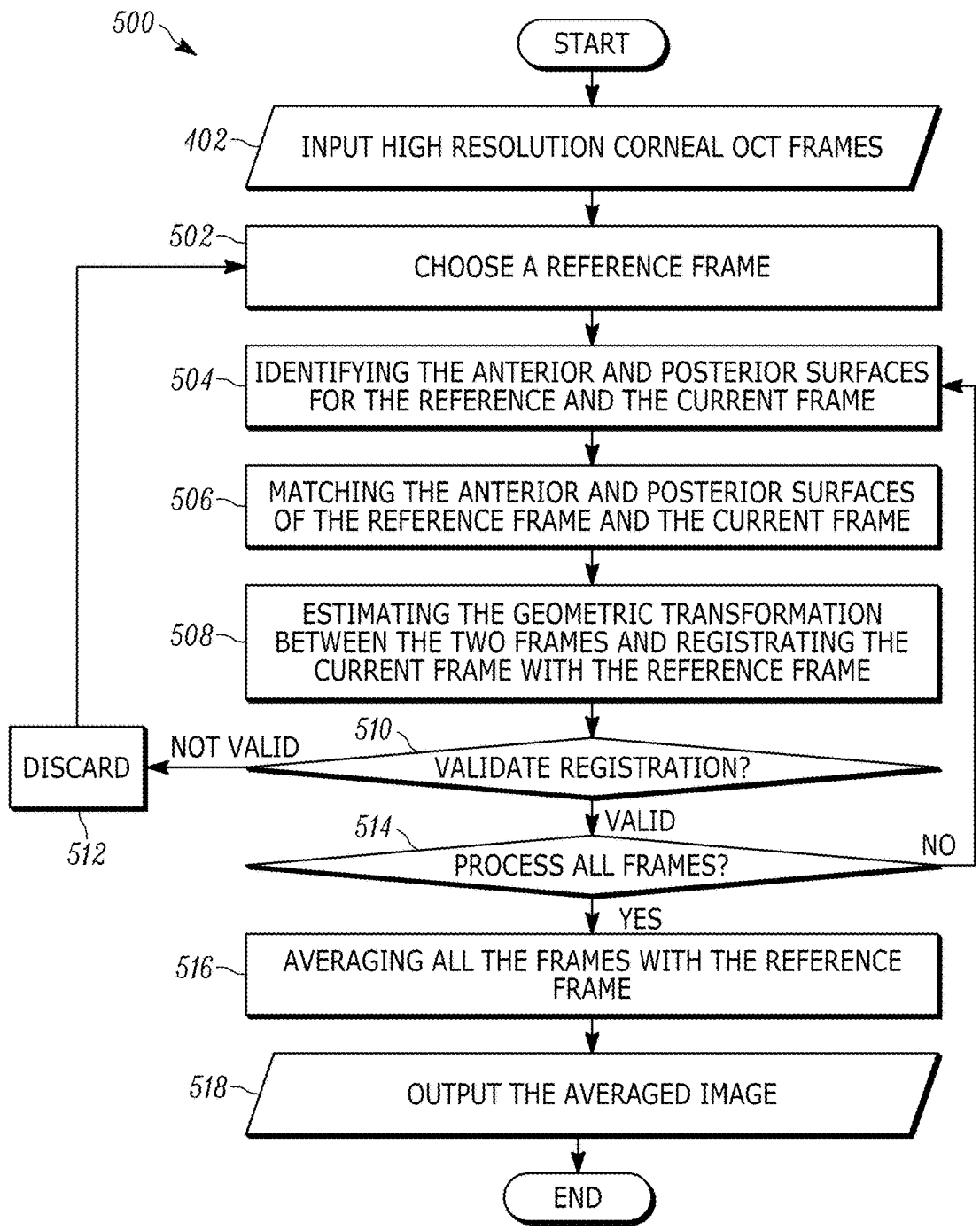
FIG. 9 illustrates a registration process that may be performed during the process of FIG. 8, in an example.
Figure 10:
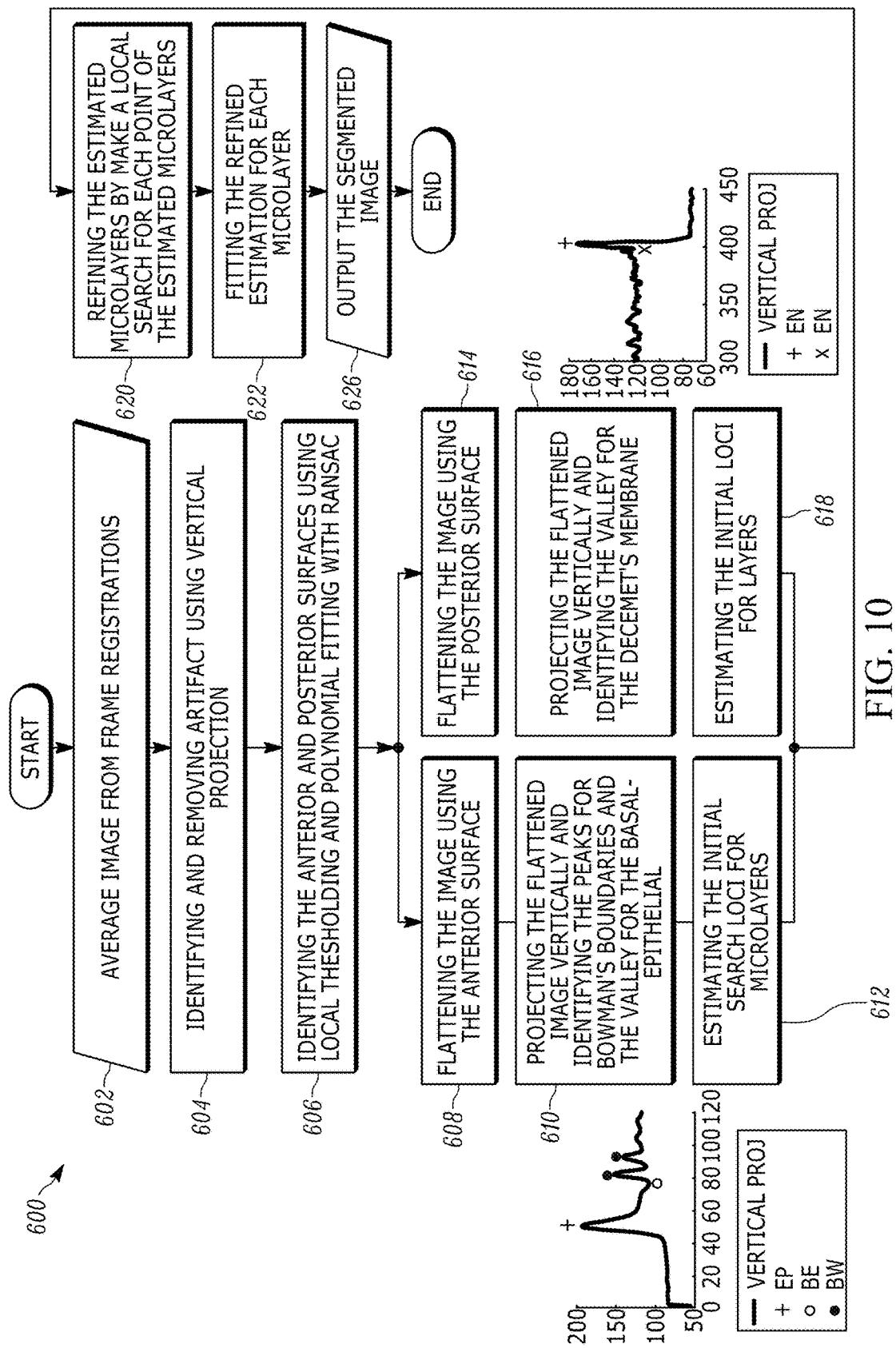
FIG. 10 illustrates a segmentation process that may be performed during the process of FIG. 8, in an example.

FIGS. 8-10 illustrate further example computer-implemented processes for evaluating the eye of a subject. As with the process 100, the process 400 may be implemented wholly or partly on an optical imaging system, such as an OCT machine, or on any suitable image process (i.e., imaging system).

In the illustrated example implementation of the process 400, high-resolution OCT images are captured at an operation 402, and an image registration is performed on the high-resolution OCT images using anterior and posterior corneal surfaces and corneal apex for alignment at an operation 404. The registration may occur between a captured reference image and subsequent captures images. For example, multiple images of the cornea may be captured for all corneal regions. Those images may be radial or raster cut images, for example. In some examples, several images of the exact same region of cornea will be captured. These captured images are registered at the operation 404. The operation 404 may register images captured for each of the regions of the cornea in this way.

Image segmentation is then performed at an operation 406. In the illustrated example, the image segmentation is performed by double flattening the image and producing an averaged image for the cornea (or, in other examples, an averaged image for reach region of the cornea) using the anterior and posterior surfaces to localize initial conditions for layers, and from there a refining segmentation of the original image is performed. In some examples, the segmentation operation is performed without the registration and/or without the averaging operations of 404. That is, operation 404 is optional. In such examples, the captured high-resolution images of operation 402 may be obtained directly by the operation 406, after capture by the optical imaging device, where segmentation and thickness mapping operations are then performed. In some implementations, the segmentation operation and further operations of process 400 are performed on one or more of the received high-resolution images from the optical imaging system.

In the illustrated example, at an operation 408, the segmented, averaged images for each corneal region are analyzed, thickness data is obtained, that data for reach corneal region is mapped into 3D points and alignment of some or all of points is performed using the apex of the anterior surface for alignment. In this way, thickness maps are formed through operations that register images using the anterior and posterior surfaces as well as the apex. By registering images using the two surfaces, in these examples, we have found that we can account for rotational motion artifacts and we can more accurately register images without flattening the image to preserve the apex of the cornea and use it to as a reference and thus compensate for lateral motion artifacts. Additionally, by aligning images using the corneal apex which represent the center of the cornea, we can correct for motion artifacts resulting from patient moving their eyes during images.

At an operation 410, interpolation is performed on the 3D points from the operation 408, and that interpolation is performed for each surface using, in this example, cubic interpolation and smoothing to obtain a final layer surface. At an operation 412, 3D refraction correction algorithm is applied on each corneal micro-layer to correct for optical distortions resulting from light refraction at different corneal interfaces with different refractive indices.

Additionally, resampling of each layer into a uniform grid may be performed at the operation 412. At operation 414, the thickness of one or more micro-layers is determined by measuring the short distance between micro-layers as the thickness. At an operation 416, the machine generates 3D thickness heat maps and a bull's-eye display for each micro-layer and displays them to an operator. For example, an operator may select which micro-layer the machine is to display, and the machine displays the corresponding 3D thickness heat map and bull's-eye display.

The processes herein, such as process 400, include a number of advantages that improve computer operation involved with cornea image processing and diagnostics. The registration operation 404, for example, is much more accurate due to the use of dedicated anterior surface and posterior surfaces on the collected images. The process is further enhanced and motion artifacts are corrected by the addition, in this example, of matching the anterior and posterior surfaces between frames. The segmentation operation 406 improves computer operation, as well, by introducing robust processing and artifact removal for corneal OCT images, through flattening the image using both the anterior and posterior surfaces, and uniquely identifying other layers from the vertical projections of the two flattened images. The segmentation also allows specific refinements such as, for vertical projection, periphery parts of the image may be excluded and the central part of the image may be excluded, but only if a central artifact is detected. Such refinements can produce enhanced peak detection, for example. Operation 414 provides further advantage, including defining the thickness as the shortest distance between each two successive micro-layers, instead of the distance measured across the normal to a surface, which can be inaccurate.

FIG. 9 illustrates an example image registration process 500 that may be performed by the operation 404 of FIG. 8. The high-resolution OCT images are obtained at the operation 402. At operation 502 a reference frame is chosen by the machine, such as the first received image, or the first received image with a determined image quality, such as with a signal-to-noise ratio above a threshold. At an operation 504, the anterior and posterior corneal surfaces of the reference image and for the current frame being compared to the reference image are determined. The anterior and posterior surfaces of both are matched to one another at an operation 506. From the matching, a geometric transformation between the two frames is estimated at an operation 508 and registration is performed based on the geometric transformation.

An operation 510 determines if the registration is valid. For example, the operation 510 may perform an automated image processing edge blur analysis and/or image contrast analysis. In some examples, an operator may subjectively assess image quality and clarity of displayed micro-layers.

If the registration is not valid, the registration is discarded at an operation 512 and the process repeats by choosing a new reference frame at operation 502. In other examples, the process may discard the registration and return to operation 504 to perform another attempted transformation and registration. In such examples, the process may return to operation 504 a given number of times, such as twice, before returning to operation 502 to determine a new reference frame. If instead, the registration is valid at operation 510, then the process (operation 514) determines if there are any more frames to process, and either returns to operation 504 or then performs an averaging of all processed frames with the reference frame at an operation 516, from which an averaged image is output at operation 518, and that averaged image is used for segmentation at operation 406.

FIG. 10 illustrates an example process 600 that may be implemented as the segmentation operation 406 of FIG. 8. In the illustrated implementation, the averaged image from the registration operation 404 is provided at operation 602. The registration and averaging processes, however, are optional and may not be performed. For example, in some implementations, the captured high-resolution images of operation 402 are passed to the operation 604 (of operation 406) after capture by the optical imaging device, bypassing the registration and averaging processes of operation 404. In any event, in the illustrated implementation, artifact identification and removal using vertical projection is performed on the averaged image at an operation 604. Anterior and posterior surfaces are identified using local thresholding and polynomial fitting from a random sample consensus (RANSAC) iterative process at an operation 606. That operation 606 leads to different operation pipes, one on each of the anterior surface and the posterior surface. For example, the image data from operation 606 may be buffered into two different identical copies each of which is analyzed on each of the two double flattening pipes illustrated. These copies may be exact duplicates of the entire corneal image, while in other examples, truncated versions of the entire corneal image may be used, an anterior rendition and a posterior rendition, respectively.

A flattening of the averaged image is performed using the anterior surface at an operation 608. Next, the flattened image is projected vertically and the peaks for the Bowman's layer boundaries are identifying and the valley for the basal-epithelial layer is identified at an operation 610. An operation 612 then estimates the initial search loci for these micro-layers. Any number of micro-layers may be identified at the operation 610, including, for example, the epithelium, the basal epithelium, the Bowman's layer, and the endothelium/Descemet's layer, by way of example.

In a separate operation, flattening of the averaged image (e.g., a copy thereof), is performed using the posterior surface by operation 614. Next, the flattened image is projected vertically to identify the valley for the Descemet's layer at an operation 616, after which the loci of the micro-layers (e.g., endothelium/Descemet's complex layer) are estimated at a block 618.

Figure 13A:
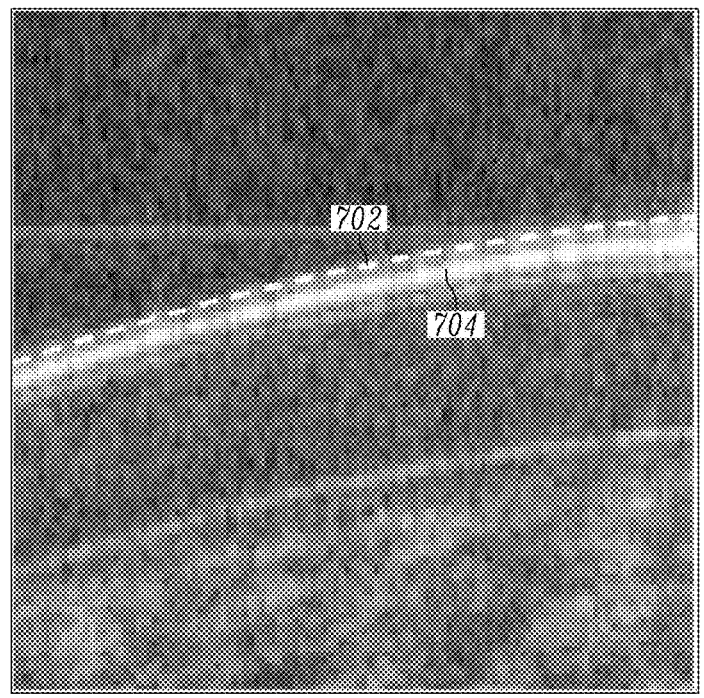
FIGS. 13A and 13B illustrate an example refinement procedure during segmentation identifying an anterior boundary of an epithelial layer, with FIG. 13A showing a segmentation line prior to refinement and FIG. 13B showing the segmentation line after refinement, in accordance with an example.
Figure 13B:
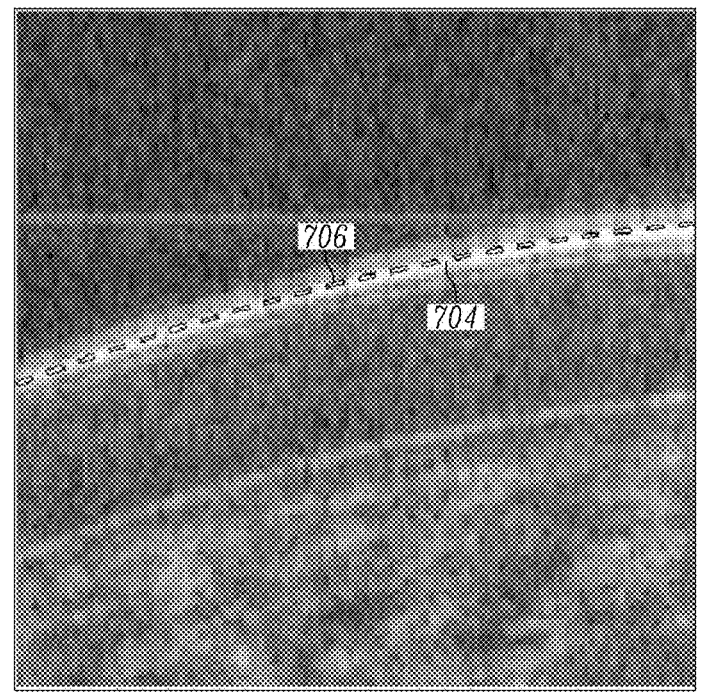
Figure 14A:
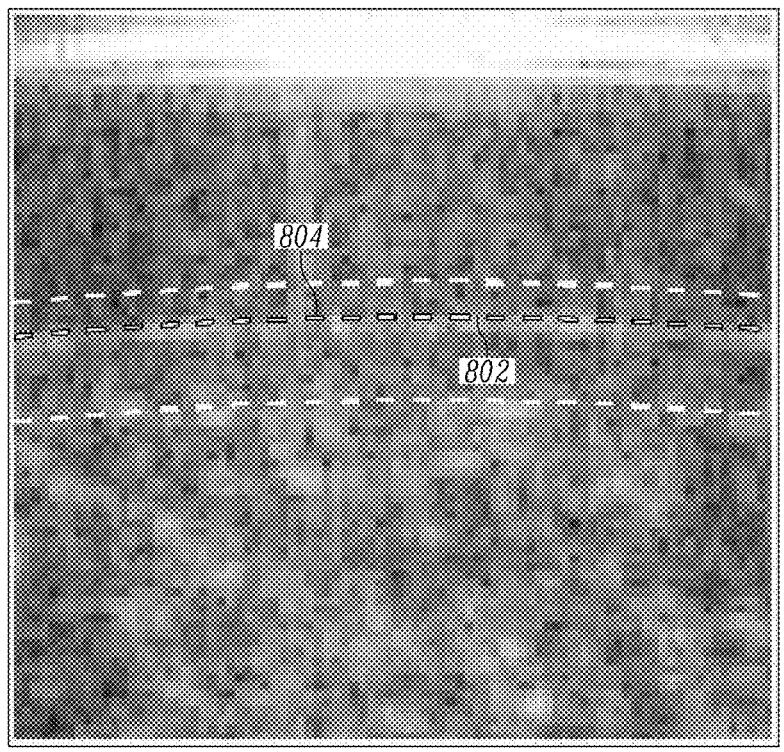
FIGS. 14A and 14B illustrate an example refinement procedure during segmentation identifying an anterior boundary of a Bowman's layer, with FIG. 14A showing a segmentation line prior to refinement and FIG. 14B showing the segmentation line after refinement, in accordance with an example.
Figure 14B:
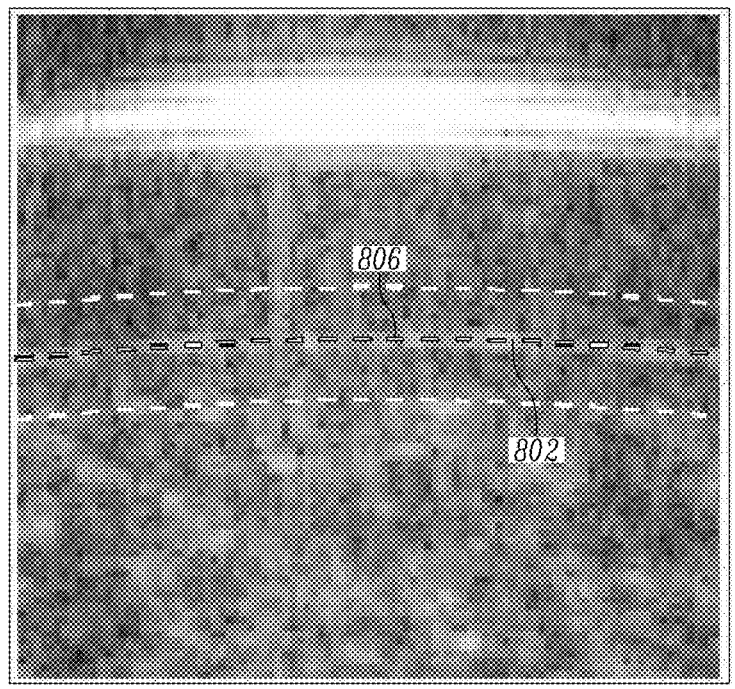

The estimated loci of micro-layers output from operations 612 and 618 (see example estimated loci plots in legends) are then combined, and an operation 620 refines the estimate micro-layers by making a local search for each point of the estimated micro-layers, e.g., the local peaks in the loci plots. At an operation 622, a fitting is performed on the refined estimation of each micro-layer identified. FIGS. 13A and 13B illustrate an example segmentation refinement for an anterior boundary of the epithelial layer, as performed by the operations 620 and 622. As shown in FIG. 13A, a high-resolution OCT image (e.g., an averaged image received at operation 602 from the frame registration process of FIG. 9) has been segmented using a double flattening process. A segmentation line 702, shown as a dashed line, and an anterior boundary of the epithelial layer 704 are illustrated. This initial segmentation line 702, while close, is slightly off-centered from the epithelial layer 704. In FIG. 13B, however, the same segmented OCT image is shown after the refining automatic segmentation operation 620. The result is a refined segmentation line 706 that more closely matches the actual anterior boundary of the epithelial layer 704. FIGS. 14A and 14B illustrate another example. A segmented OCT image is shown of an anterior boundary 802 of a Bowman's layer. An initial segmentation line 804 is shown in FIG. 14A, while a refined segmentation line 806, after the operations 620, is shown in FIG. 14B. In some example implementations, a refinement process is performed on each of the images, and where the initial segmentation was accurate, the refinement will not result in changes to the segmentation.

In an example, the operation 620 refines the micro-layers segmentation by making a local search for each point of the estimated micro-layers, e.g., the local peaks in the loci plots forming the segmentation line. The initial segmented image from the double flattening process, e.g., combining the two pipeline images, is analyzed by the system to search locally for the best alternative for each point in the estimated initial guess of the micro-layer boundaries (i.e., the initial guess of the segmentation lines in FIGS. 13A and 14A). These micro-layer boundary estimates are processed in order to ensure that there is no overlapping or crossing between layers and each micro-layer search window is limited by its predecessor and successor micro-layers. In an example, the initial segmentation line is filtered using a proposed filter given by $$\frac{1}{16} * \begin{bmatrix} 1 & 1 & 1 \\ 1 & 8 & 1 \\ 1 & 1 & 1 \end{bmatrix}.$$

This filter takes the mean of the 8-neighbors of the center pixel of a segmentation line and then averages it with the center pixel to give more emphasis on the center pixel of that segmentation line. The result is $$\frac{1}{16} * \begin{bmatrix} 1 & 1 & 1 \\ 1 & 8 & 1 \\ 1 & 1 & 1 \end{bmatrix} = \frac{1}{2}\left(\frac{1}{8} * \begin{bmatrix} 1 & 1 & 1 \\ 1 & 0 & 1 \\ 1 & 1 & 1 \end{bmatrix} + \begin{bmatrix} 0 & 0 & 0 \\ 0 & 1 & 0 \\ 0 & 0 & 0 \end{bmatrix}\right).$$

To reduce the effect of speckle noise or background noise, the refined segmentation lines are smoothed with a median and moving average filters or fitted to a second order polynomial. As a result, the segmentation line is more accurately matched to the micro-layer boundary.

In some examples, after the operation 620, a graphs search (GS) technique or a Randomized Hough Transform (RHT) technique was used to further strengthen segmentation. For the GS technique, a graph of the segmented image was constructed, each pixel in the image was considered as a node in the graph, and the system calculated an edge between these nodes based on their gray-values and their gradient. Then, when searching for a specific interface, the system only examined the points in this search region, which reduced the search time and increased the accuracy. Once a path of minimum weight was found by the system, it was declared as the interface in this region. The same procedure was done for all interfaces. Thus, in this example implementation of GS, modifications were done in the construction of the graph such as the definition of the start node and the end done, the edge weights, and the connectivity between nodes.

In RHT technique, the unknown parameters of a model were detected by the system from points potentially fitting the model using a voting scheme. For the RHT technique, a second order polynomial model was used (y=ax2+bx+c with the unknown parameters a, b, and c). The RHT technique then transformed each point from the Cartesian space (x, y) into the parameter space (a, b, c), where points voted for every possible value of the parameters in a finite range. The vote, performed by the system, was done using the gray-value of the point. Finally, points in the parameter space that had maximum votes were chosen as the parameters value for the used model. To speed up the vote process, only the highest gray-value points were used by the system. Thus, in this example implementation, the system used RHT, a second order polynomial model, and did not use any prior knowledge.

The refinement operations 620 and 622 are optional and may not be performed in some examples. Either way, the resulting segmented image is output at an operation 624, after which control may be passed to operation 410.

EXAMPLES

The present techniques were implemented in a number of empirical studies.

In one study, the techniques were applied on OCT images of 5 normal eyes to automatically segment, and create the 3D Endothelium/Descemet's membrane Complex (En/DM) micro-layer color coded and bull's-eye maps. Maps were divided into different regions. En/DM mean thickness in normal subjects was 16.19 μm. En/DM showed thickening towards the peripheral cornea. The mean thickness of the central En/DM was 11±2 μm (Mean and SD), paracentral En/DM region was 12±2.75 μm and the peripheral En/DM was 15.5±4.75 μm. The study showed that in normal Subjects, En/DM showed relative thickening towards the peripheral cornea.

In one study, the techniques were used to evaluate using En/DM 3D micro-layer tomography maps to diagnose Fuchs endothelial dystrophy. We imaged 27 eyes of 23 individuals (11 Fuchs' endothelial dystrophy eyes in 7 patients; 16 control eyes) using OCT. En/DM layer was segmented using the automatic segmentation method. 3D En/DM Color coded and bull's-eye micro-layer tomography thickness maps were created and divided into different regions. In Fuchs' endothelial dystrophy eyes, En/DM 3D micro-layer tomography maps showed significant thickening as compared to controls. In Fuchs endothelial dystrophy eyes, mean thickness was 25, 27 & 31 μm in central, paracentral and peripheral zones versus 12, 13 & 15 μm, respectively, in controls (P<0.0001). The En/DM map showed relative thickening towards the periphery in both control and Fuchs' patients (P=0.045 & P<0.0001 respectively). The study showed, for the first time, that En/DM 3D micro-layer tomography maps show significant thickening in Fuchs endothelial dystrophy, as compared to controls.

In one study, the techniques were used to create color coded and bull's-eye maps of En/DM layer in patients with graft rejection and compare them to control eyes. The study demonstrated that En/DM 3D micro-layer tomography maps show significant thickening in corneal graft rejection as compared to control eyes. In this prospective interventional case series, 22 eyes with corneal grafts post penetrating Keratoplasty (PKP) and Descemet Stripping Automated Endothelial Keratoplasty (DSAEK; 17 clear, and 5 rejected corneal grafts) were imaged using OCT. The micro-layers of the cornea were segmented automatically. Color coded 3D thickness and bull's-eye maps of the layer were created. With the techniques, we were able to create 3D color coded micro-layer tomography maps and bull's-eye maps of the layer for all included eyes. The mean thickness of En/DM on the bull's-eye were 20.15±5.66, 23.16±7.01, 28.57±10.45 versus 41.44±21.96, 47.71±23.45 and 59.20±25.65 μm for central, paracentral and peripheral regions in clear graft versus rejected graft, respectively. The study showed specific thickening in rejected grafts when compared to clear graft.

In one study, the techniques were used to create 3D micro-layer thickness color coded and bull's-eye maps of the corneal basal epithelial layer (B-Epi) and reported the thickness data of 12 normal subjects. Images were obtained using an OCT and corneal layers were then segmented. A refraction correction algorithm was used to correct optical distortions. 3D micro-layer tomography thickness maps (C-MLT) were generated. One patient with limbal stem cell dystrophy (LSCD) was imaged for comparison. The thickness of B-Epi was found to be uniform between the center, mid-periphery and periphery with means of 12.2+1.8, 12.5+1.9 & 13.3+2.2 μm, respectively. The thickness of the B-Epi positively correlated, showing significance, with corneal epithelium (p<0.0001, R=0.64). Weak correlation between of the B-Epi and the corneal thickness was demonstrated (p=0.003, R=0.2). The patient with LSCD exhibited an attenuated B-Epi and complete absence of the layer in the left eye. The study showed that corneal micro-layer tomography 3-D thickness maps (C-MLT) provide a tool to study the basal layer of the epithelium. C-MLT disclosed that this layer is uniform across the cornea, and correlates with epithelial and total corneal thickness. The study showed that patients with LSCD have an attenuated layer.

In one study, the techniques were used to create 3D Bowman's layer micro-layer optical coherence tomography maps (e.g., heat maps or bull's-eye maps) for normal subjects. 13 normal eyes were imaged using OCT. Segmentation method were employed to automatically segmented the micro-layers of the cornea. Corneal micro-layer surfaces were reconstructed and a refraction correction algorithm were used to correct optical distortions. Color coded 3D and bull's-eye thickness maps of the layer were created. Using our technique, we were able to create the micro-layer and bull's-eye maps of the layer for all included eyes. Bull's-eye map was divided to different regions (specifically, using the mapping of FIG. 11). The mean thickness data on the bull's-eye of normal subjects were 19±1, 19±1, 20±2, 20±3, 21±2, 20±1, 20±3, 20±2, 23±2, 24±4, 24±4, 23±3, 24±4, 25±4 um for C1, C2, M1, M2, M3, M4, M5, M6, O1, O2, O3, O4, O5, O6, respectively. Peripheral BL was significantly thicker than the mid-peripheral regions (P<0.001). Both peripheral and middle regions' Bowman's Layer were significantly thicker than the central region's Bowman's Layer (P<0.001). There was a weak positive correlation between Bowman's Layer thickness and total corneal thickness (R=0.3, P<0.001). The study showed that in normal subjects, Bowman's Layer significantly thickens as the layer progresses from the center to the periphery.

In one study, the techniques were used to create 3-Dimensional Bowman's layer micro-layer tomography maps (e.g., heat maps or bull's-eye maps) and evaluated the use of the created maps for diagnosing keratoconus (KC). 30 eyes (15 KC and 15 controls) were imaged using OCT with scanning protocol to image the BL over a 9 mm diameter zone of the cornea. Images were analyzed to segment the Bowman's Layer producing a 9 mm color coded Bowman's layer micro-layer tomography maps. Receiver operating characteristic curves were created to evaluate their diagnostic accuracy. Bowman's Layer 3D micro-layer tomography maps disclosed significant Bowman's Layer thinning in KC eyes compared to controls (P<0.001). Bowman's Layer thinning in inferior half of the cornea had excellent accuracy in diagnosing KC with an area under the curve of 1 (P<0.001). Bowman's Layer thickness was less than 14 m in the inferior half of the cornea was 100% sensitive and specific in diagnosing KC. The study showed that Bowman's Layer 3D extra wide micro-layer tomography map has excellent accuracy, sensitivity and specificity in diagnosing keratoconus.

In one study, the techniques were used to create Bowman's micro-layer tomography 3-dimensional (3D) maps (e.g., heat maps or bull's-eye maps) in the diagnosis of subclinical keratoconus (KC). 40 eyes (17 normal and 23 subclinical KC) were imaged using OCT. Subclinical KC was defined as patients with normal clinical examination and Placido topography (TMS-3; Tomey, Erlangen, Germany) but abnormal elevation tomography (Pentacam; Oculus, Wetzlar, Germany). The techniques segmented Bowman's layer (BL). Segmentations were reconstructed to produce Bowman's layer color-coded 3D micro-layer thickness and bull's-eye maps. Bull's-eye maps were divided into 14 different regions (see, e.g., FIG. 11) and Bowman's layer thickness was calculated for each region and compared between groups. Bowman's layer color-coded 3D micro-layer thickness and bull's-eye maps were successfully created for all studied eyes. In subclinical KC, Bowman's layer color-coded 3D micro-layer thickness and bull's-eye maps disclosed localized relative thinning of Bowman's layer. In subclinical KC, Bowman's layer minimum thickness was significantly less in C1, C2, C5 regions (p<0.01). We concluded that Bowman's layer color-coded 3D micro-layer thickness and bull's-eye maps techniques may be used for diagnosis of subclinical keratoconus. Bowman's layer color-coded 3D micro-layer thickness and bull's-eye maps disclosed a significant localized relative thinning that can be quantified using our maps.

The study also showed that Bowman's Ectasia index (BEI), an index from the first patent, calculated in each segment of the 3D map was diagnostic of subclinical KC. Bowman Ectasia index (BEI) were calculated for each region and compared between groups. As discussed above, the BEI was defined as minimum thickness of BL in each region of the inferior cornea divided by the mean thickness of BL in the corresponding region of the superior cornea multiplied by 100. The study found that BEI was significantly lower in subclinical KC as compared to normal eyes in region C1, C2, M1, M2, M4, M5, M6, O4 and O5 (70±11, 70±12, 72±12, 71±11, 73±13, 62±19, 71±13, 66±19, 60±20 µm vs. 83±8, 83±11, 80±9, 81±9, 82±8, 80±11, 80±12, 78±15, 78±20 µm; P<0.05).

In one study, the techniques were used to generate 3D maps of the Bowman's layer for a patient with post-refractive surgery ectasia. The techniques were used to analyze images and segment the Bowman's layer and produce 3D color coded Bowman's layer tomography maps (e.g., heat maps or bull's-eye maps). The 3D color coded and bull's-eye map of Bowman's layer disclosed pathological thinning of the layer. Thus the study showed that 3D Bowman's micro-layer tomography map may be used in diagnosing post-refractive surgery ectasia.

In another study, we imaged patient with dry eye syndrome and normal patient using OCT. 3D color coded and bull's-eye maps were generated using the present techniques. The Epithelial micro-layer corneal tomography map disclosed that the epithelium is highly irregular as compared to the normal subject.

The techniques herein were also used to examine, for the first time, collagen crosslinking (CXL). CXL is a treatment modality for progressive corneal ectasia. CXL has proven to strengthen the corneal tissue by forming new covalent bonds between collagen fibers. It was noted that the treatment leads to development of a demarcation line in the cornea, that is, hyper-reflective areas of the cornea that are said to represent the transition zone between the crosslinked and the untreated cornea. That transition zone is a measurement of the depth of CXL treatment into the cornea and thus a measurement of its effectiveness. The present techniques were used to create a 3D total corneal collagen crosslinking demarcation band micro-layer tomography maps (e.g., heat maps or bull's-eye maps), which our studies show correlate with the localized effect of treatment on the cornea.

In one study, 18 eyes with progressive keratoconus underwent corneal CXL. In 1 month postoperatively, OCT maps were captured and analyzed with the system to create 3D corneal collagen crosslinking demarcation band maps (CXL-OCT), see, e.g., FIGS. 15A-15C. Correlation between demarcation band characteristics on CXL-OCT and corneal curvature changes captured using Pentacam tomography were evaluated.

Figure 15A:
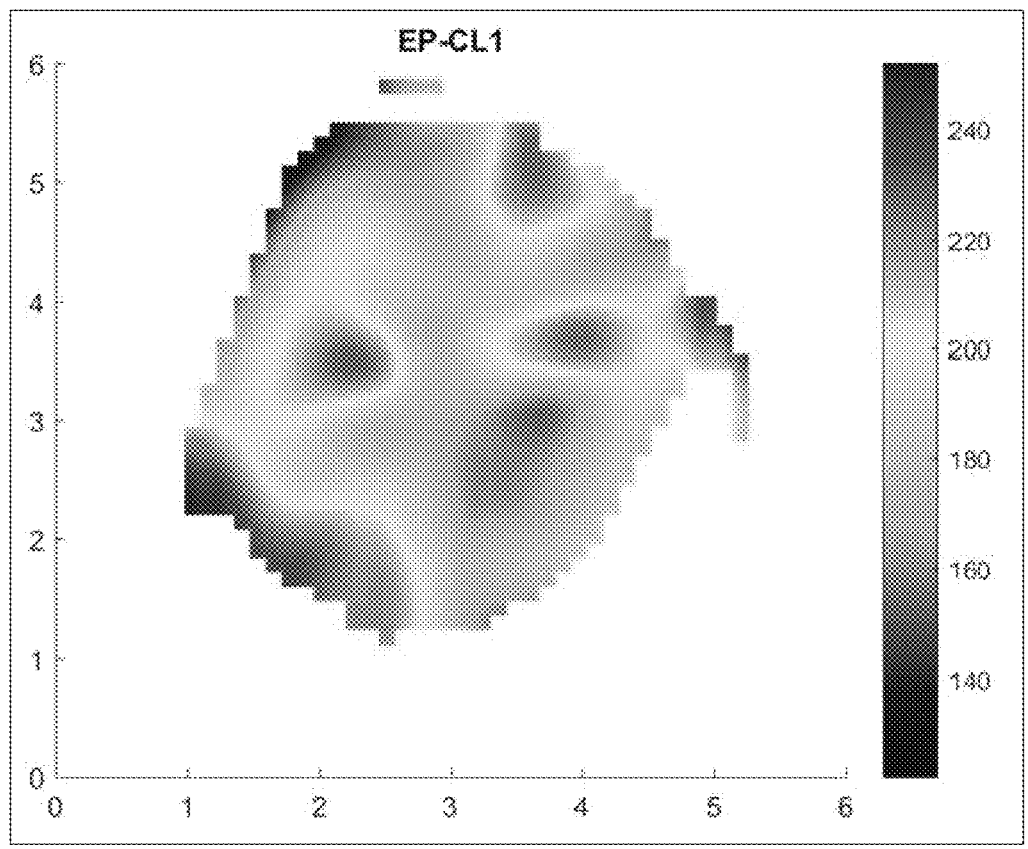
FIG. 15A illustrates a heat map showing the depth of a collagen crosslinking micro-layer within the cornea measured from the epithelium, in accordance with an example.
Figure 15B:
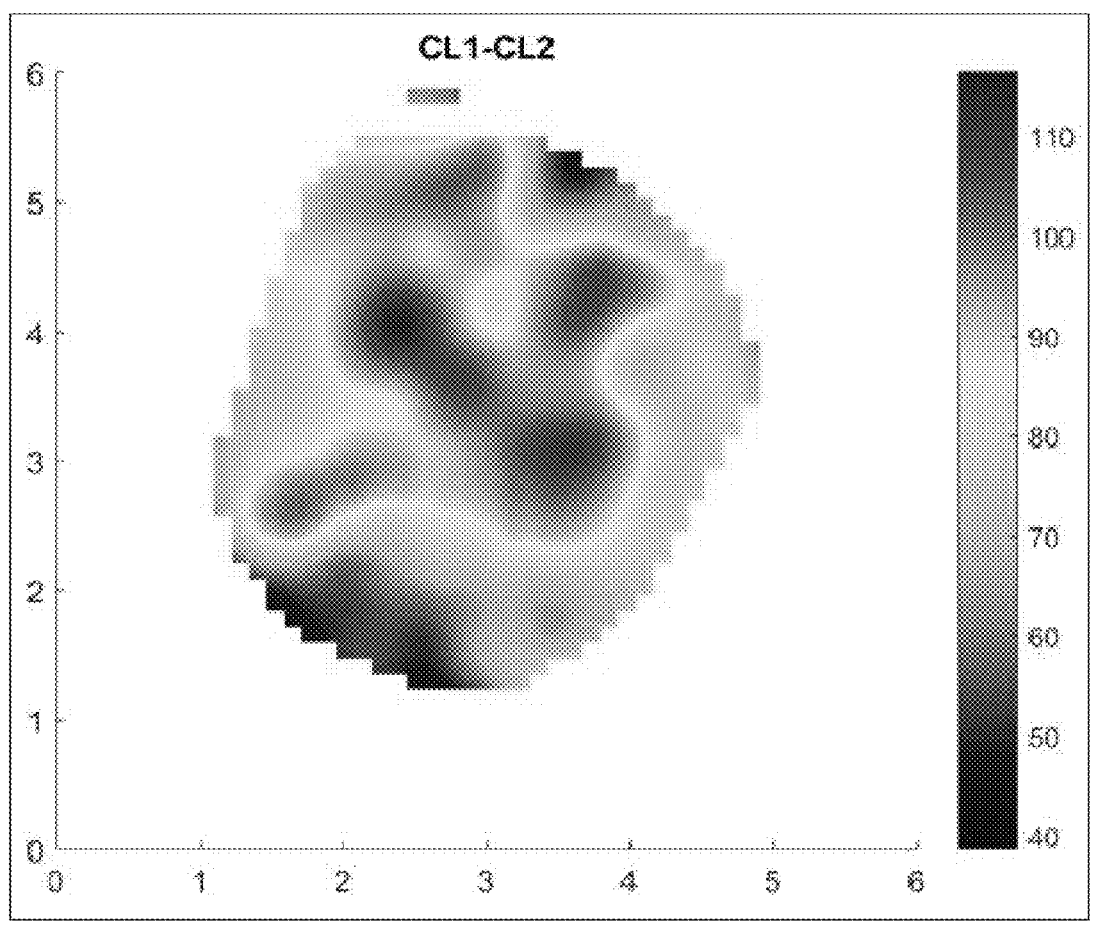
FIG. 15B illustrates a thickness heat map of a collagen crosslinking micro-layer within the cornea, in accordance with an example.
Figure 15C:
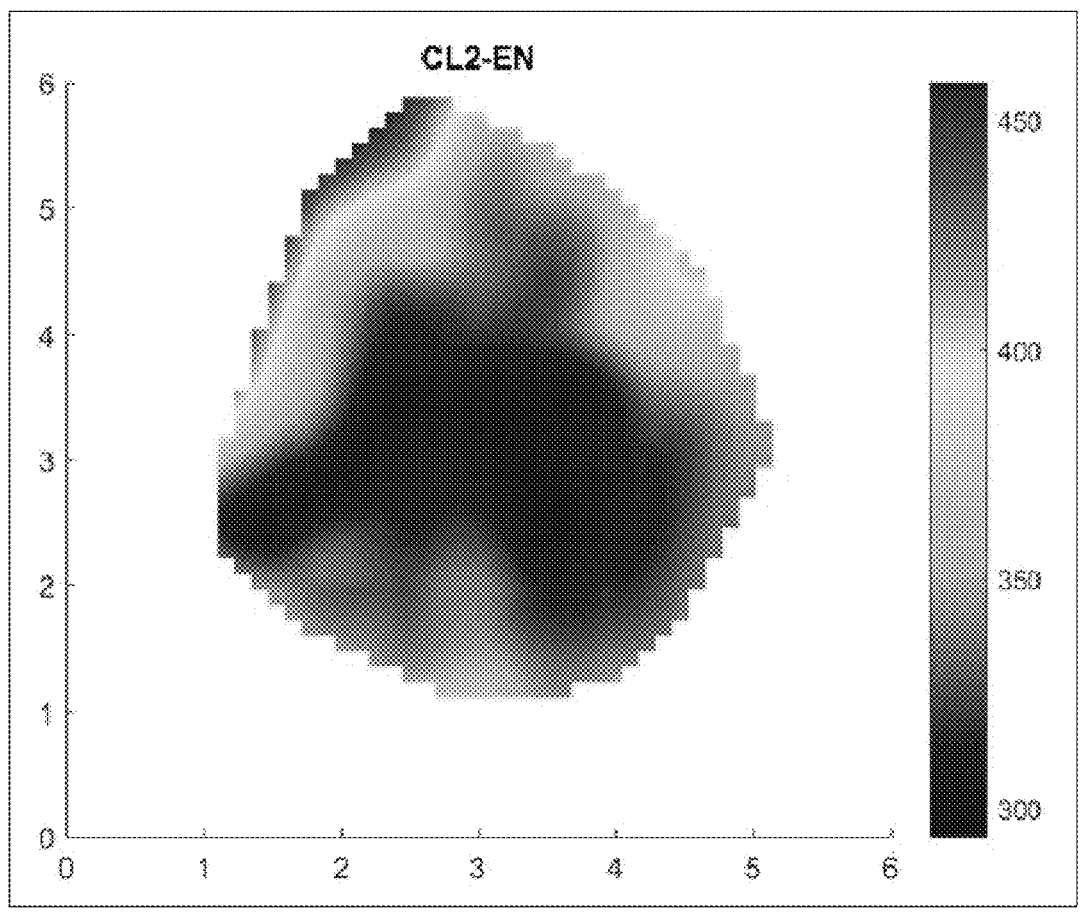
FIG. 15C illustrates a heat map showing a distance between a collagen crosslinking micro-layer within the cornea and the endothelium, in accordance with an example.

Using the present techniques, we were able to generate CXL-OCT maps for all patients. The mean thickness (FIG. 15B) and depth (FIG. 15A) of CXL demarcation bands were 77±35 µm and 279±82 µm, respectively. CXL demarcation bands maps were significantly thicker in central cornea compared to paracentral and peripheral cornea (91±31, 74±34, and 63±35 µm, respectively; p<0.01) (FIG. 15B). There was no significant difference between the depth of CXL demarcation band maps in different corneal regions (FIG. 15A). Significant positive correlation was noted between CXL demarcation band depth and postoperative flattening effect in the inferior cornea (R=0.4, P<0.05) as disclosed using the CXL-OCT. Thus the study showed that the deeper the localized demarcation band on the CXL-OCT maps, the more the localized postoperative flattening effect is.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A computer-implemented method of evaluating an eye, the method comprising:
   segmenting, using an image processor, a plurality of high-resolution images of a cornea of the eye, to identify one or more of the plurality of biologically-defined micro-layers of the cornea, the plurality of high-resolution images comprising a plurality of images for a plurality of biologically-defined micro-layers of the cornea;
   determining thickness data for each of the identified one or more of the plurality of biologically-defined micro-layers, from the segmentation of the plurality of high-resolution images;
   developing, from the thickness data for each of the identified one or more of the plurality of biologically-defined micro-layers, a thickness map, the thickness map identifying differences in corneal thickness across the identified biologically-defined micro-layer; and
   displaying the thickness map, wherein the thickness map comprises one of:
   (i) a bull's-eye map of micro-layer thickness mean, variance, and standard deviation;
   (ii) a bull's-eye map or heat map of a ratio or comparison of micro-layer thickness to a total corneal thickness;
   (iii) a bull's-eye map of a ratio or comparison of thickness of the micro-layer to normative data;
   (iv) a bull's-eye map of a ratio or comparison between micro-layer thickness of a region to the thickness of the micro-layer in another region;
   (v) a heat map of a ratio between micro-layer thickness of a region to the thickness of the micro-layer in another region;
   (vi) a heat map or bulls-eye map of basal epithelial layer, the heat map having a color coding that differentiates minimum thickness regions of the basal epithelial layer, normal thickness regions of the basal epithelial layer, and maximum thickness regions of the basal epithelial layer; or
   (vii) a heat map or bull's-eye map of a collagen cross-linking layer.

2. The method of claim 1, wherein the identified one or more of the plurality biologically-defined micro-layers comprises
an epithelium,
a basal epithelial layer,
a Bowman's layer,
one or more endothelial/Descemet's layers complex, and/or
a collagen crosslinking layer.

3. The method of claim 1, wherein the plurality of high-resolution images comprises
(i) a plurality of images of the cornea each captured with the eye looking in a different direction, where a wide scan of the cornea is formed by stitching images together, or
(ii) a plurality of wide scan images of the cornea corrected for optical distortion.

4. The method of claim 1, wherein the plurality of high-resolution images comprises images of the cornea captured from a wide angle lens capture of the optical imaging system.

5. The method of claim 1, wherein the thickness map is correlated to a diagnosable condition of the cornea, wherein the diagnosable condition is selected from the group consisting of keratoconus, pellucid marginal degeneration, post-refractive surgery ectasia, corneal transplant rejection and corneal transplant failed grafts, Fuchs dystrophy, limbal stem cell deficiency, dry eye syndrome, and post-operative collagen crosslinking procedure.

6. The method of claim 1, wherein the thickness map is correlated to a diagnosable condition of the cornea, wherein the diagnosable condition comprises keratoconus, pellucid marginal degeneration, and/or post-refractive surgery ectasia, and wherein the identified one or more of the plurality biologically-defined micro-layers comprises the Bowman's layer, wherein the thickness map comprises:
(i) bull's-eye map of a ratio or comparison of thickness of the micro-layer to normative data, wherein the bull's-eye map is of a ratio or comparison between measured thickness of the Bowman's layer corresponding to a bull's-eye section and normal thickness of the Bowman's layer,
(ii) the heat map of a ratio between micro-layer thickness of a region to the thickness of the micro-layer in another region, wherein the heat map is of a ratio between measured thickness and normal thickness of the Bowman's layer, or
(iii) the bull's-eye map of a ratio or comparison between micro-layer thickness of a region to the thickness of the micro-layer in another region, wherein the bull's-eye map is of a ratio or comparison between measured thickness in a region of the Bowman's layer corresponding to a bull's-eye section and that measured in another region of the Bowman's layer.

7. The method of claim 1, wherein the thickness map is correlated to a diagnosable condition of the cornea, wherein the diagnosable condition comprises Fuchs dystrophy and/or corneal graft health, rejection and failure, and wherein the identified one or more of the plurality biologically-defined micro-layers comprises Endothelium/Descemet's layer of the cornea, wherein the thickness map comprises:
(i) the bull's-eye map of a ratio or comparison of thickness of the micro-layer to normative data, wherein the bull's-eye map is of a ratio or comparison between measured thickness of the Endothelium/Descemet's layer corresponding to a bull's-eye section and normal thickness of the Endothelium/Descemet's layer,
(ii) the heat map of a ratio between micro-layer thickness of a region to the thickness of the micro-layer in another region, wherein the heat map is of a ratio between measured thickness and normal thickness of the Endothelium/Descemet's layer, or
(iii) the bull's-eye map of a ratio or comparison between micro-layer thickness of a region to the thickness of the micro-layer in another region, wherein the bull's-eye map is of a ratio or comparison between measured thickness in a region of the Endothelium/Descemet's layer corresponding to a bull's-eye section and that measured in another region of the Endothelium/Descemet's layer.

8. The method of claim 1, wherein the thickness map is correlated to a diagnosable condition of the cornea, wherein the diagnosable condition comprises dry eye, and wherein the identified one or more of the plurality biologically-defined micro-layers comprises an epithelium, a basal epithelial layer, a Bowman's layer, and one or more endothelial/Descemet's layers complex of the cornea, wherein the thickness map comprises the bull's-eye map of a ratio or comparison between micro-layer thickness of a region to the thickness of the micro-layer in another region, wherein the bull's-eye map is of the corneal epithelium including an irregularity indication of changes in thickness across the corneal epithelium corresponding to a bull's-eye section that indicates differences in concentration of thickness irregularities across different regions of the cornea.

9. The method of claim 8, wherein the different regions of the corneal epithelium comprise
(1) a central portion of the cornea corresponding to the diagnosable condition being aqueous deficiency,
(2) a lower or upper portion of the cornea corresponding to the diagnosable condition being lipid deficiency dry eye syndrome or Meibomian gland dysfunction.

10. The method of claim 1, wherein the thickness map is correlated to a diagnosable condition of the cornea, wherein the diagnosable condition comprises limbal stem cell deficiency, basal epithelial cells thinning, or absence indicates corneal limbal stem cell deficiency, and wherein the identified one or more of the plurality biologically-defined micro-layers of the cornea comprises basal epithelial layer, wherein the thickness map comprises the bull's-eye map or heat map of the basal epithelial layer having a color coding that differentiates minimum thickness regions of the basal epithelial layer, normal thickness regions of the basal epithelial layer, and maximum thickness regions of the basal epithelial layer.

11. The method of claim 1, wherein segmenting the plurality of high-resolution images, to identify image data for each of the plurality of biologically-defined micro-layers of the cornea further comprises:
(a) performing an image registration on the plurality of high-resolution images by
(i) identifying an anterior surface of one of the plurality of biologically-defined micro-layers of the cornea, the anterior surface being a registration reference surface,
(ii) comparing a plurality of image frames in the plurality of high-resolution images to the anterior surface,
(iii) extracting frames that do not satisfy a registration condition, and
(iv) for the remaining frames performing a summation and averaging process to produce a high-resolution composite image of the one of the plurality of biologically-defined micro-layers.

12. The method of claim 11, further comprising:
(b) identifying one or more contrast transition surfaces for the high-resolution composite image, the transition surfaces corresponding to interfaces between the different corneal micro-layers;
(c) performing (a) for an adjacent biologically-defined micro-layer to identify a second high-resolution composite image, the adjacent biologically-defined micro-layer being identified by the one or more contrast transition surfaces; and
(d) performing (c) for each biologically-defined micro-layer of the cornea.

13. The method of claim 12, wherein (b) is performed to identify a transition to an anterior interface of the epithelium, an epithelium/basal epithelial layer interface, a basal epithelium/Bowman's interface, Bowman's/stroma interface, an anterior interface of the endothelial/Descemet's layers, an interface of the endothelial/Descemet's layers, an aqueous humor, and/or a collagen crosslinking layer interface.

14. The method of claim 1, wherein segmenting the plurality of high-resolution images further comprises:
(a) performing an image registration on the plurality of high-resolution images by, for each of the plurality of high-resolution images,
 (i) identifying an anterior surface of the cornea and a posterior surface of the cornea, and
 (ii) matching the anterior surface of the cornea and the posterior surface of the cornea to an anterior surface and a posterior surface, respectively, of a reference frame; and
(b) performing a summation and averaging process to produce a high-resolution composite image from the registered plurality of high-resolution images, where the high-resolution composite image is of the cornea.

15. The method of claim 14, wherein performing the image registration on the plurality of high-resolution images further comprises, for each of the plurality of high-resolution images, identifying an apex of the cornea and matching the apex of the cornea to an apex of a reference frame.

16. The method of claim 14, wherein segmenting the plurality of high-resolution images further comprises:
identifying an anterior surface and a posterior surface of the high-resolution composite image;
flattening the high-resolution composite image using the anterior surface;
flattening the high-resolution composite image using the posterior surface;
estimating one or more biologically-defined micro-layers of the cornea from the flattening using the anterior surface;
estimating one or more the biologically-defined micro-layers of the cornea from the flattening using the posterior surface; and
generating a segmented high-resolution composite image by combining the estimating from the flattening using the anterior surface with the estimating from the flattening using the posterior surface.

17. The method of claim 16, wherein estimating one or more biologically-defined micro-layers of the cornea from the flattening using the anterior surface comprises
performing a vertical projection of the flattening using the anterior surface and identifying one or more contrast transition surfaces corresponding to interfaces between the one or more biologically-defined micro-layers; and wherein estimating one or more biologically-defined micro-layers of the cornea from the flattening using the posterior surface comprises performing a vertical projection of the flattening using the posterior surface and identifying one or more contrast transition surfaces corresponding to interfaces between the one or more biologically-defined micro-layers.

18. The method of claim 17, wherein the one or more contrast transition surfaces corresponding to an anterior interface of the epithelium, an epithelium/basal epithelial layer interface, a basal epithelium/Bowman's interface, Bowman's/stroma interface, an anterior interface of the endothelial/Descemet's layers, a posterior interface of the endothelial/Descemet's layers, an aqueous humor interface, and/or a collagen crosslinking layer interface.

19. A system comprising:
one or more processors;
a computer-readable memory storing non-transient instructions that when executed by the one or more processors cause the system to:
segment, using an image processor, a plurality of high-resolution images of a cornea of the eye, to identify one or more of the plurality of biologically-defined micro-layers of the cornea, the plurality of high-resolution images comprising a plurality of images for a plurality of biologically-defined micro-layers of the cornea, the segmentation causing the system to:
 (a) perform an image registration on the plurality of high-resolution images by (i) identifying an anterior surface of one of the plurality of biologically-defined micro-layers of the cornea, the anterior surface being a registration reference surface, (ii) comparing a plurality of image frames in the plurality of high-resolution images to the anterior surface, (iii) extracting frames that do not satisfy a registration condition, and (iv) for the remaining frames performing a summation and averaging process to produce a high-resolution composite image of the one of the plurality of biologically-defined micro-layers;
 (b) identify one or more contrast transition surfaces for the high-resolution composite image, the transition surfaces corresponding to interfaces between the different corneal micro-layers; and
 (c) perform (a) for an adjacent biologically-defined micro-layer to produce a second high-resolution composite image, the adjacent biologically-defined micro-layer being identified by the one or more contrast transition surfaces;
determine thickness data for each of the identified one or more of the plurality of biologically-defined micro-layers, from the segmentation of the plurality of high-resolution images;
develop, from the thickness data for each of the identified one or more of the plurality of biologically-defined micro-layers, a thickness map, the thickness map identifying differences in corneal thickness across the identified biologically-defined micro-layer; and
display the thickness map.

20. The system of claim 19, wherein (b) is performed to identify a transition to an anterior interface of the epithelium, an epithelium/basal epithelial layer interface, a basal epithelium/Bowman's interface, Bowman's/stroma interface, an anterior interface of the endothelial/Descemet's layers, an interface of the endothelial/Descemet's layers, an aqueous humor, and/or a collagen crosslinking layer interface, wherein (c) is performed for each biologically-defined micro-layer of the cornea.

21. A system comprising:
one or more processors;
a computer-readable memory storing non-transient instructions that when executed by the one or more processors cause the system to:
perform a two-surface registration on each of a plurality of high-resolution images of the cornea, the plurality of high-resolution images comprising a plurality of images for a plurality of biologically-defined micro-layers of the cornea, and generate a high-resolution composite image of the cornea, wherein the two-surface registration comprises an anterior surface registration and a posterior surface registration;
segment the high-resolution composite image to identify each of the plurality of biologically-defined micro-layers of the cornea, wherein segmentation of the high-resolution composite image comprises flattening the high-resolution composite image and performing a vertical projection of a flattened rendition of the high-resolution composite image to produce a segmented high-resolution composite image;
determine the thickness of at least one of the plurality of biologically-defined micro-layers of the cornea from the segmented high-resolution composite image;
develop a thickness map for at least one of the plurality of biologically-defined micro-layers of the cornea, the thickness map identifying visual differences in thickness across the at least one of the plurality of biologically-defined micro-layers; and
display the thickness map.

22. The system of claim 21, wherein the computer-readable memory stores further non-transient instructions that when executed by the one or more processors cause the system to:
(a) perform the image registration on the plurality of high-resolution images by, for each of the plurality of high-resolution images, (i) identifying an anterior surface of the cornea and a posterior surface of the cornea, and (ii) matching the anterior surface of the cornea and the posterior surface of the cornea to an anterior surface and a posterior surface, respectively, of a reference frame; and
(b) perform a summation and averaging process to produce a high-resolution composite image from the registered plurality of high-resolution images, where the high-resolution composite image is of the cornea.

23. The system of claim 22, wherein the computer-readable memory stores further non-transient instructions that when executed by the one or more processors cause the system to:
perform the image registration on the plurality of high-resolution images by identifying an apex of the cornea and matching the apex of the cornea to an apex of a reference frame.

24. A system comprising:
one or more processors;
a computer-readable memory storing non-transient instructions that when executed by the one or more processors cause the system to:
perform an image registration on a plurality of high-resolution images of a cornea to generate a high-resolution composite image of the cornea from a plurality of high-resolution images of the cornea, the plurality of high-resolution images comprising a plurality of images for a plurality of biologically-defined micro-layers of the cornea;
segment the high-resolution composite image to identify each of the plurality of biologically-defined micro-layers of the cornea using a multiple surface flattening on the high-resolution composite image, the segmentation generating a segmented high-resolution composite image;
determine the thickness of at least one of the plurality of biologically-defined micro-layers of the cornea from the segmented high-resolution composite image;
develop a thickness map for the at least one of the plurality of biologically-defined micro-layers of the cornea, the thickness map identifying visual differences in thickness across the at least one of the plurality of biologically-defined micro-layers; and
display the thickness map.

25. The system of claim 24, wherein the non-transient instructions that when executed by the one or more processors cause the system to segment the high-resolution composite image to identify each of the plurality of biologically-defined micro-layers of the cornea using a multiple surface flattening on the high-resolution composite image, cause the system to:
identify an anterior surface and a posterior surface of the high-resolution composite image;
flatten the high-resolution composite image using the anterior surface;
flatten the high-resolution composite image using the posterior surface;
estimate one or more biologically-defined micro-layers of the cornea from the flattening using the anterior surface;
estimate one or more biologically-defined micro-layers of the cornea from the flattening using the posterior surface; and
generate a segmented high-resolution composite image by combining the estimating from the flattening using the anterior surface with the estimating from the flattening using the posterior surface.

26. The system of claim 25, wherein the computer-readable memory stores further non-transient instructions that when executed by the one or more processors cause the system to:
estimate the one or more biologically-defined micro-layers of the cornea from the flattening using the anterior surface by performing a vertical projection of the flattening using the anterior surface and identifying one or more contrast transition surfaces corresponding to interfaces between the one or more biologically-defined micro-layers; and
estimate the one or more biologically-defined micro-layers of the cornea from the flattening using the posterior surface by performing a vertical projection of the flattening using the posterior surface and identifying one or more contrast transition surfaces corresponding to interfaces between the one or more biologically-defined micro-layers.

27. The system of claim 24, wherein the image registration is a multiple surface registration, and wherein the plurality of high-resolution images comprise images of the cornea, each being curved images with an apex.

* * * * *

UNITED STATES PATENT AND TRADEMARK OFFICE
CERTIFICATE OF CORRECTION

| | |
|---|---|
| PATENT NO. | : 10,368,735 B2 |
| APPLICATION NO. | : 15/868856 |
| DATED | : August 6, 2019 |
| INVENTOR(S) | : Mohamed Abou Shousha and Amr Saad Mohamed Elsawy |

Page 1 of 1

It is certified that error appears in the above-identified patent and that said Letters Patent is hereby corrected as shown below:

In the Specification

Column 1, Lines 18 to 21, under the heading STATEMENT OF GOVERNMENT SUPPORT, cancel the text "This invention was made with government support under Grant No. K23EY026118 awarded by the National Eye Institute. The Government has certain rights in the invention." and insert the following:
--This invention was made with government support under EY026118 awarded by National Institutes of Health. The government has certain rights in the invention.--

Signed and Sealed this
Twenty-second Day of November, 2022

Katherine Kelly Vidal
*Director of the United States Patent and Trademark Office*